US010085752B2

(12) United States Patent
Williams et al.

(10) Patent No.: US 10,085,752 B2
(45) Date of Patent: Oct. 2, 2018

(54) APPARATUS FOR ENDOSCOPIC PROCEDURES

(71) Applicant: Covidien LP, Mansfield, MA (US)

(72) Inventors: Justin Williams, Southbury, CT (US); Paul Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 172 days.

(21) Appl. No.: 15/271,588

(22) Filed: Sep. 21, 2016

(65) Prior Publication Data

US 2017/0007252 A1   Jan. 12, 2017

Related U.S. Application Data

(62) Division of application No. 13/799,379, filed on Mar. 13, 2013, now Pat. No. 9,492,189.

(51) Int. Cl.
*A61B 17/072* (2006.01)
*A61B 17/29* (2006.01)
(Continued)

(52) U.S. Cl.
CPC ...... *A61B 17/07207* (2013.01); *A61B 1/0057* (2013.01); *A61B 17/00234* (2013.01);
(Continued)

(58) Field of Classification Search
CPC ............... A61B 17/068; A61B 17/072; A61B 17/07207; A61B 17/32002; A61B 1/0052;
(Continued)

(56) References Cited

U.S. PATENT DOCUMENTS 2,777,340 A   1/1957   Hettwer et al.
2,957,353 A   10/1960   Babacz
(Continued)

FOREIGN PATENT DOCUMENTS

AU   2008229795 A1   4/2009
CA      2451558 A1   1/2003
(Continued)

OTHER PUBLICATIONS

Extended European Search Report corresponding to International Application No. EP 15 19 0760.7 dated Apr. 1, 2016.
(Continued)

*Primary Examiner* — Scott A. Smith

(57) ABSTRACT

An electromechanical surgical device is provided and includes an end effector configured to perform at least one function; and a shaft assembly. The end effector includes a rotatable drive screw having a coupling member at a proximal end thereof; and a flexible drive cable rotatably supported therein and extending therefrom, wherein the flexible drive cable receives rotational forces and transmits said rotational forces to the drive screw to actuate the end effector. The shaft assembly includes a proximal neck housing supported at a distal end of the outer tube; and a distal neck housing pivotally connected to the proximal neck housing, wherein a distal end of the distal neck housing is configured and adapted for operative connection with the end effector. In use, when the end effector is connected to the shaft assembly, the flexible drive cable extends through the proximal neck housing and the distal neck housing.

20 Claims, 21 Drawing Sheets

(51) Int. Cl.
*A61B 17/28* (2006.01)
*A61B 17/068* (2006.01)
*A61B 1/005* (2006.01)
*A61B 17/00* (2006.01)

(52) U.S. Cl.
CPC .......... *A61B 17/068* (2013.01); *A61B 17/072* (2013.01); *A61B 17/282* (2013.01); *A61B 17/29* (2013.01); *A61B 2017/0046* (2013.01); *A61B 2017/00398* (2013.01); *A61B 2017/00473* (2013.01); *A61B 2017/00477* (2013.01); *A61B 2017/00734* (2013.01); *A61B 2017/07214* (2013.01); *A61B 2017/07285* (2013.01); *A61B 2017/2903* (2013.01); *A61B 2017/2927* (2013.01)

(58) Field of Classification Search
CPC ........ A61B 1/0057; A61B 2017/00327; A61B 2017/00398; A61B 2017/2927; A61B 2017/2903; A61B 2017/2238; A61B 2017/00314; A61B 2017/07214; A61B 2017/07285
USPC .. 227/19, 175.1, 175.2, 178.1, 180.1, 176.1; 606/139, 151, 153, 213, 219, 143
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |

(56) References Cited

U.S. PATENT DOCUMENTS

| | | |
|---|---|---|
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm |
| 7,588,176 B2 | 9/2009 | Timm |
| 7,637,409 B2 | 12/2009 | Marczyk |
| 7,641,093 B2 | 1/2010 | Doll et al. |
| 7,644,848 B2 | 1/2010 | Swayze |
| 7,670,334 B2 | 3/2010 | Hueil |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,568,444 B2 | 10/2013 | Cunningham |
| 8,623,000 B2 | 1/2014 | Humayun et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,696,552 B2 | 4/2014 | Whitman |
| 8,708,213 B2 | 4/2014 | Shelton, IV et al. |
| 8,746,529 B2 | 6/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,911,471 B2 | 12/2014 | Spivey et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,991,677 B2 | 3/2015 | Moore et al. |
| 8,992,422 B2 | 3/2015 | Spivey et al. |
| 9,044,230 B2 | 6/2015 | Morgan et al. |
| 9,064,653 B2 | 6/2015 | Prest et al. |
| 9,101,358 B2 | 8/2015 | Kerr et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,492,189 B2 | 11/2016 | Williams et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0055411 A1 | 3/2003 | Whitman et al. |
| 2003/0165794 A1 | 9/2003 | Matoba |
| 2004/0094597 A1 | 5/2004 | Whitman et al. |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia |
| 2006/0142656 A1 | 6/2006 | Malackowski et al. |
| 2006/0142740 A1 | 6/2006 | Sherman et al. |
| 2006/0259073 A1 | 11/2006 | Miyamoto et al. |
| 2006/0278680 A1 | 12/2006 | Viola et al. |

(56) References Cited

U.S. PATENT DOCUMENTS

| | | |
|---|---|---|
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0276430 A1* | 11/2007 | Lee .................... A61B 1/00071 606/205 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0171147 A1 | 7/2009 | Lee et al. |
| 2009/0182193 A1 | 7/2009 | Whitman et al. |
| 2009/0206138 A1 | 8/2009 | Smith et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184459 A1* | 7/2011 | Malkowski ............ A61B 17/29 606/206 |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0096457 A1* | 4/2013 | Qiu ........................ A61B 1/267 600/549 |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2014/0110455 A1 | 4/2014 | Ingmanson et al. |
| 2014/0207125 A1 | 7/2014 | Applegate et al. |
| 2014/0207182 A1 | 7/2014 | Lergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Lergiebel et al. |
| 2015/0048144 A1 | 2/2015 | Whitman |
| 2015/0052798 A1* | 2/2015 | Kovarik ................ A01K 77/00 43/8 |
| 2015/0076205 A1 | 3/2015 | Lergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101507625 A | 8/2009 |
| CN | 101856251 A | 10/2010 |
| CN | 101909526 A | 12/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |

(56) References Cited

FOREIGN PATENT DOCUMENTS

| | | | |
|---|---|---|---|
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08038488 | 2/1996 |
| JP | 2005125075 A | 5/2005 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 2003065916 A1 | 8/2003 |
| WO | 03077769 A1 | 9/2003 |
| WO | 2003090630 A2 | 11/2003 |
| WO | 2004-032762 A1 | 4/2004 |
| WO | 2004107989 A1 | 12/2004 |
| WO | 06042210 A2 | 4/2006 |
| WO | 2007016290 A2 | 2/2007 |
| WO | 2007026354 A1 | 3/2007 |
| WO | 2007137304 A2 | 11/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009088430 A1 | 7/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |

OTHER PUBLICATIONS

Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Extended European Search Report from Appl. No. EP 16198094.1 dated Feb. 2, 2017.
Chinese Office Action and English translation from Appl. No. 2014100931376.6 dated Mar. 13, 2017.
Australian Examination Report No. 1 issued in Appl. No. AU 2014200778 dated May 16, 2017.
Japanese Office Action, and English langue translation, issued in Appl. No. JP 2014-047757 dated Oct. 12, 2017 (10 pages).
European search Report from Appl. No. 13177163.6 dated Nov. 15, 2013. (8 pages).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Partial European Search Report from Application No. EP 14159056.2 dated Jun. 18, 2014 (8 pp).
U.S. Appl. No. 13/769,419, filed Feb. 18, 2013, Williams et al.
International Search Report corresponding to PCT/US2005/027266, completed May 30, 2008 and dated Jun. 18, 2008; (2 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
European Search Report No. 14159056.2 dated Sep. 17, 2014.
European Examination Report corresponding to EP 14159056.2 dated Oct. 26, 2015.
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).

(56) References Cited

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Japanese Office Action dated Jun. 29, 2018 issued in corresponding JP Appln. No. 2014-047757.

\* cited by examiner

_US 10,085,752 B2_

APPARATUS FOR ENDOSCOPIC PROCEDURES

CROSS-REFERENCE TO RELATED APPLICATION

The present application is a divisional of U.S. patent application Ser. No. 13/799,379, filed Mar. 13, 2013, now U.S. Pat. No. 9,492,189, the entire disclosure of which is incorporated by reference herein.

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

Many of these electromechanical surgical devices are relatively expensive to manufacture, purchase and/or operate. There is a constant desire by manufactures and end users to develop electromechanical surgical devices that are relatively inexpensive to manufacture, purchase and/or operate yet still provide a large degree of operability.

Accordingly, a need exists for electromechanical surgical apparatus, devices and/or systems that are relatively economical from the development and manufacturing stages, to the selling/purchase stages, to the storing/shipping stages, to the use/operation stages, and on to the disposal and/or re-use stages while still providing an end user with a high degree of operability.

SUMMARY

The present disclosure relates to electromechanical, hand-held surgical apparatus, devices and/or systems configured for use with removable disposable loading units and/or single use loading units for clamping, cutting and/or stapling tissue.

According to an aspect of the present disclosure, an electromechanical surgical device is provided. The electromechanical surgical device includes an end effector configured to perform at least one function. The end effector includes a rotatable drive screw having a coupling member at a proximal end thereof; and a flexible drive cable rotatably supported therein and extending therefrom, wherein the flexible drive cable receives rotational forces and transmits said rotational forces to the drive screw to actuate the end effector. The electromechanical surgical device includes a shaft assembly. The shaft assembly includes a proximal neck housing supported at a distal end of the outer tube; and a distal neck housing pivotally connected to the proximal neck housing, wherein a distal end of the distal neck housing is configured and adapted for operative connection with the end effector. In use, when the end effector is connected to the shaft assembly, the flexible drive cable extends through the proximal neck housing and the distal neck housing.

The shaft assembly may include a coupling lug extending distally from the distal neck housing. The coupling lug may be located substantially along a central longitudinal axis of the shaft assembly.

The end effector may define a central opening formed in a proximal surface thereof. The central opening of the end effector may be configured and dimensioned to receive the coupling lug of the shaft assembly when the end effector is connected to the shaft assembly.

The end effector may include a lock actuator having at least a first position and a second position. In use, when the lock actuator is in the first position the coupling lug of the shaft assembly may be insertable into the central opening of the end effector upon a connection of the end effector to the shaft assembly.

In use, when the lock actuator is in the second position the coupling lug of the shaft assembly may be prevented from insertion into the central opening of the end effector. In use, when the end effector is coupled to the shaft assembly, a disposition of the lock actuator to the second position may secure the end effector to the shaft assembly to inhibit disconnection of the end effector from the shaft assembly.

The end effector may include a lock bar operatively engageable by the lock actuator. The lock bar may include a first position in which the lock bar does not extend across the central opening of the end effector; and a second position in which the lock bar at least partially extends across the central opening of the end effector.

The lock actuator may urge the lock bar to the second position when the lock actuator is in the second condition.

The coupling lug may define an outer annular race therearound. In use, when the lock bar is in the second position, and when the end effector is coupled to the shaft assembly, the lock bar may at least partially enter the annular race of the coupling lug.

The lock actuator may be biased to the second position or the lock bar may be biased to the first position.

The lock actuator may include an intermediate position between the first position and the second position thereof. In use, when the lock actuator is in the intermediate position, an angled camming surface of the lock actuator may be in contact with the lock bar such that the lock bar is disposed at an intermediate position between the first position and the second position thereof.

In use, in the intermediate position of the lock actuator, upon a separation of the end effector from the shaft assembly, the coupling lug of the end effector may exert a force on the lock bar to urge the lock bar to the second position and the lock actuator to the first position.

The shaft assembly may define at least a pair of distally oriented notches formed in a distal end thereof. The pair of notches may be radially offset by about 90° relative to one another. In use, the end effector may be rotated relative to the shaft assembly to axially align the lock actuator with one of the pair of notches to fix a rotational orientation of the end effector relative to the shaft assembly when the lock actuator is in the second position.

In use, the end effector may be arranged to be manually rotated relative to the shaft assembly.

The shaft assembly may further include an articulation bar at least partially slidably supported in the distal neck housing. The articulation bar may include a distal end; and a proximal end operatively connected to a rotatable drive shaft; wherein the articulation bar is offset a radial distance from the central longitudinal axis of the shaft assembly. The shaft assembly may further include an articulation link having a proximal end pivotally connected to the distal end of the articulation bar, and a distal end pivotally connected to the distal neck housing.

In use, actuation of the rotatable drive shaft of the electromechanical surgical device that is connected to the articulation bar may cause the articulation bar to axially translate. In use, axial translation of the articulation bar may cause the distal neck housing to pivot off axis relative to the proximal neck housing.

The shaft assembly may include a coil spring extending between and across the distal neck housing and the proximal neck housing. In use, when the end effector is connected to the shaft assembly, the flexible drive cable may be sheathed in the coil spring.

When the end effector is connected to the shaft assembly, at least the distal end of the flexible drive cable may be offset a radial distance from a central longitudinal axis of the shaft assembly.

According to another aspect of the present disclosure, an end effector for performing a surgical function and being connectable to an electromechanical power source is provided. The end effector includes an upper jaw and a lower jaw, at least one of the upper jaw and the lower jaw being movable in relation to the other of the upper jaw and the lower jaw, wherein the lower jaw of the end effector is configured to selectively receive a cartridge assembly; a drive beam slidably supported in the lower jaw and being translatable through each of the upper jaw and the lower jaw to move the lower jaw relative to the upper; a cartridge assembly configured for loading into the lower jaw, the cartridge assembly including an actuation sled slidably supported therein and being configured to expel at least a portion of a plurality of staples loaded in the cartridge assembly upon a distal movement of the actuation sled from a proximal-most position; a drive screw rotatably supported in the lower jaw, wherein the drive beam is threadably supported on the drive screw, whereby rotation of the drive screw results in axial translation of the drive beam, wherein the drive screw defines a proximal coupling socket; a proximal coupling hub defining a proximal facing opening; and a lock actuator having at least a first position and a second position; and a lock bar supported in the proximal coupling hub and being operatively engageable by the lock actuator.

The lock bar includes a first position in which the lock bar does not extend across the opening of the proximal coupling hub; and a second position in which the lock bar at least partially extends across the opening of the proximal coupling hub.

In use, when the lock actuator is in the first position the lock bar may be in the first position, and, wherein when the lock actuator is in the second position the lock bar is engaged by the lock actuator and urged by the lock actuator to the second position.

In use, either the lock actuator may be biased to the second position or the lock bar may be biased to the first position.

The lock actuator may include an intermediate position between the first position and the second position thereof. In use, when in the intermediate position, an angled camming surface of the lock actuator may be in contact with the lock bar such that the lock bar is disposed at an intermediate position between the first position and the second position thereof.

The end effector may further comprises a flexible drive cable rotatably supported therein and extending therefrom the coupling socket of the drive screw, wherein the flexible drive cable receives rotational forces and transmits said rotational forces to the drive screw to actuate the end effector.

According to a further aspect of the present disclosure, an adapter shaft assembly for selectively interconnecting an end effector and an electromechanical power source is provided. The adapter shaft assembly includes an adapter housing configured and adapted for selective connection to at least one rotatable drive shaft of the electromechanical power source; an outer tube having a proximal end supported by the adapter housing and a distal end configured and adapted for operative connection with the end effector; and at least one force transmitting assembly for interconnecting a respective one of the at least one rotatable drive shaft of the electromechanical power source and at least one rotation receiving member supported in the end effector.

The at least one force transmitting assembly includes a flexible drive cable extending from the end effector, the flexible drive cable having a first end that is connected to a rotatable drive shaft that is connected to the at least one rotatable drive shaft of the electromechanical power source and a second end that is connectable to the at least one rotation receiving member of the end effector, wherein the at least one force transmitting assembly transmits a rotation of the rotatable drive shaft of the electromechanical power source to the at least one rotation receiving member of the end effector.

The adapter shaft assembly may further comprise a proximal neck housing supported at a distal end of the outer tube; and a distal neck housing pivotally connected to the proximal neck housing, wherein a distal end of the distal neck housing is configured and adapted for operative connection with the end effector. The flexible drive cable may extend at least through the proximal neck housing and the distal neck housing when the end effector is connected to the shaft assembly.

The flexible drive cable may be offset a radial distance from a central longitudinal axis of the shaft assembly when the end effector is connected to the shaft assembly.

The adapter shaft assembly may further comprise a coupling lug extending distally from the distal neck housing. The coupling lug may be located substantially along a central longitudinal axis of the shaft assembly. The coupling lug may define an outer annular race therearound.

The distal neck housing may define at least a pair of distally oriented notches formed in a distal end thereof. The pair of notches may be radially offset by about 90° relative to one another. The end effector may be rotated relative to the shaft assembly to axially align a lock actuator of the end effector with one of the pair of notches to fix a rotational orientation of the end effector relative to the shaft assembly when the lock actuator is in a locking position projecting from the end effector.

The adapter shaft assembly may further comprise an articulation bar at least partially slidably supported in the distal neck housing. The articulation bar includes a distal end; and a proximal end operatively connected to a rotatable drive shaft; wherein the articulation bar is offset a radial distance from the central longitudinal axis of the shaft assembly.

The adapter assembly may further comprise an articulation link having a proximal end pivotally connected to the distal end of the articulation bar, and a distal end pivotally connected to the distal neck housing. In use, actuation of the at least one rotatable drive shaft of the electromechanical power source that is connected to the articulation bar may cause the articulation bar to axially translate. In use, axial translation of the articulation bar may cause the distal neck housing to pivot off axis relative to the proximal neck housing.

The shaft assembly may include a coil spring, and wherein, when the end effector is connected to the shaft assembly, the flexible drive cable may be sheathed in the coil spring.

According to still another aspect of the present disclosure, an end effector for performing a surgical function and being connectable to an electromechanical power source. The end effector comprises an upper jaw and a lower jaw, at least one of the upper jaw and the lower jaw being movable in relation to the other of the upper jaw and the lower jaw, wherein the lower jaw of the end effector is configured to selectively receive a cartridge assembly; a drive beam slidably supported in the lower jaw and being translatable through each of the upper jaw and the lower jaw to move the lower jaw relative to the upper; a drive screw rotatably supported in the lower jaw, wherein the drive beam is threadably supported on the drive screw, whereby rotation of the drive screw results in axial translation of the drive beam, wherein the drive screw defines a proximal coupling socket; and a flexible drive cable having a first end that is connectable to a rotatable drive shaft that is connected to at least one rotatable drive shaft of an electromechanical power source, and a second end that is connected to the proximal coupling socket of the drive screw, wherein the flexible drive cable transmits a rotation of the rotatable drive shaft of the electromechanical power source to the drive screw of the end effector.

The end effector may further comprise a cartridge assembly configured for loading into the lower jaw. The cartridge assembly may include an actuation sled slidably supported therein and being configured to expel at least a portion of a plurality of staples loaded in the cartridge assembly upon a distal movement of the actuation sled from a proximal-most position.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
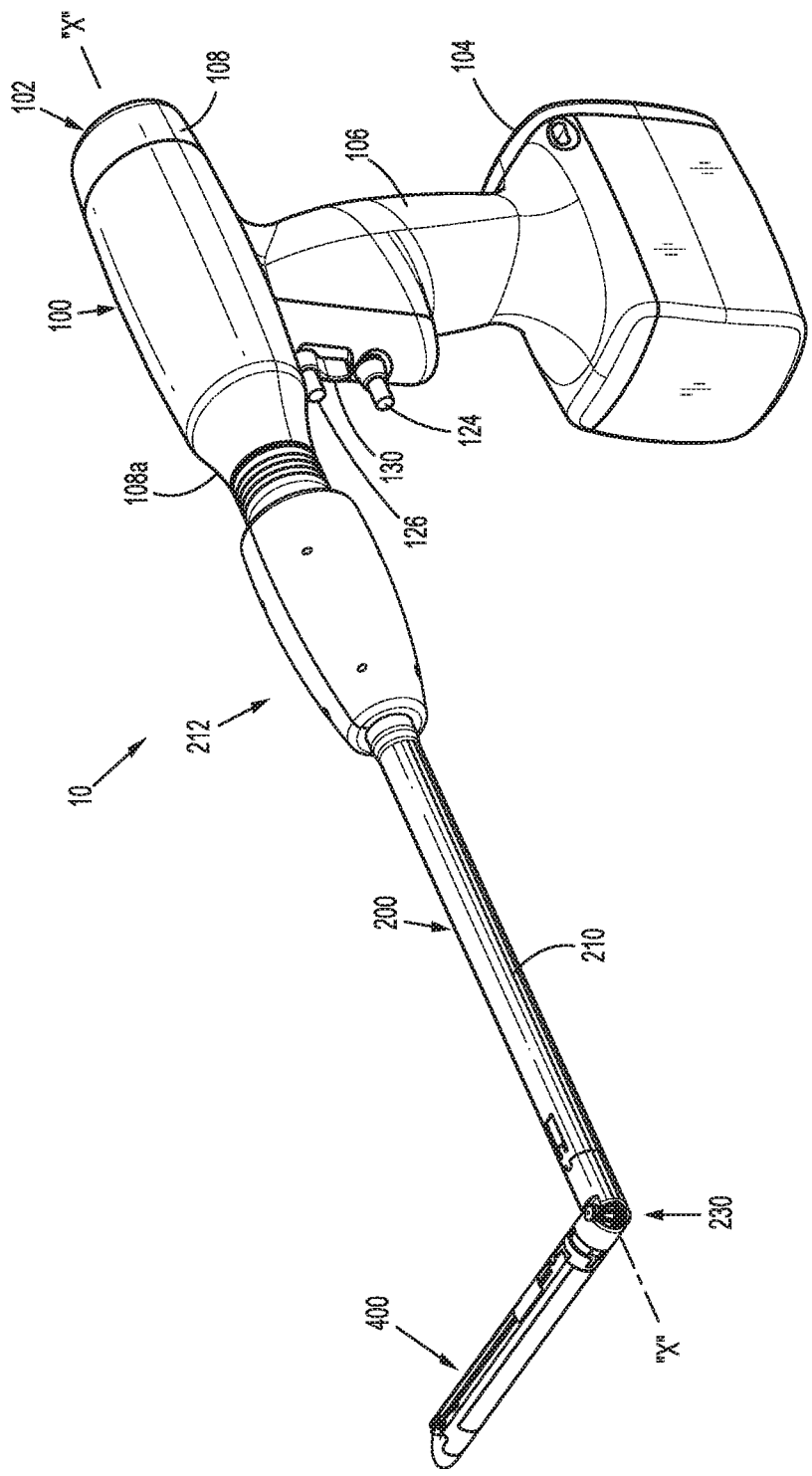
FIG. 1 is a perspective view of an electromechanical surgical system according to an embodiment of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Referring initially to FIGS. 1-4, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment with a plurality of different end effectors 400, via an adapter or shaft assembly 200, that is configured for actuation and manipulation by the electromechanical, hand-held, powered surgical instrument 100. In particular, surgical instrument 100 is configured for selective connection with shaft assembly 200, and, in turn, shaft assembly 200 is configured for selective connection with any one of a plurality of different end effectors 400. Other configurations are contemplated, such as, for example, an end effector attached to a shaft that is not removable, a remote power source and/or motor, and configurations including integral or remote computerized control.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which being hereby incorporated herein by reference, for a detailed description of the construction and operation of exemplary electromechanical, hand-held, powered surgical instrument 100. The instrument 100 may include one or more motors powered by a battery, generator, or electrical power socket.

Generally, as illustrated in FIGS. 1-4, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Handle housing 102 defines a cavity therein in which a circuit board or controller 150 and a drive mechanism 160 are situated. Drive mechanism 160 may include a first motor 164 used to select a rotatable drive member of surgical instrument 100, and a second motor 166 used to drive each rotatable drive member of surgical instrument 100.

Circuit board 150 is configured to control the various operations of surgical instrument 100. In accordance with the present disclosure, handle housing 102 provides a housing in which a rechargeable battery 156, is removably situated. Battery 156 is configured to supply power to any of the electrical components of surgical instrument 100. While a battery 156 is shown and contemplated, any known power source may be used, such as, for example a power cord or the like.

Figure 3:
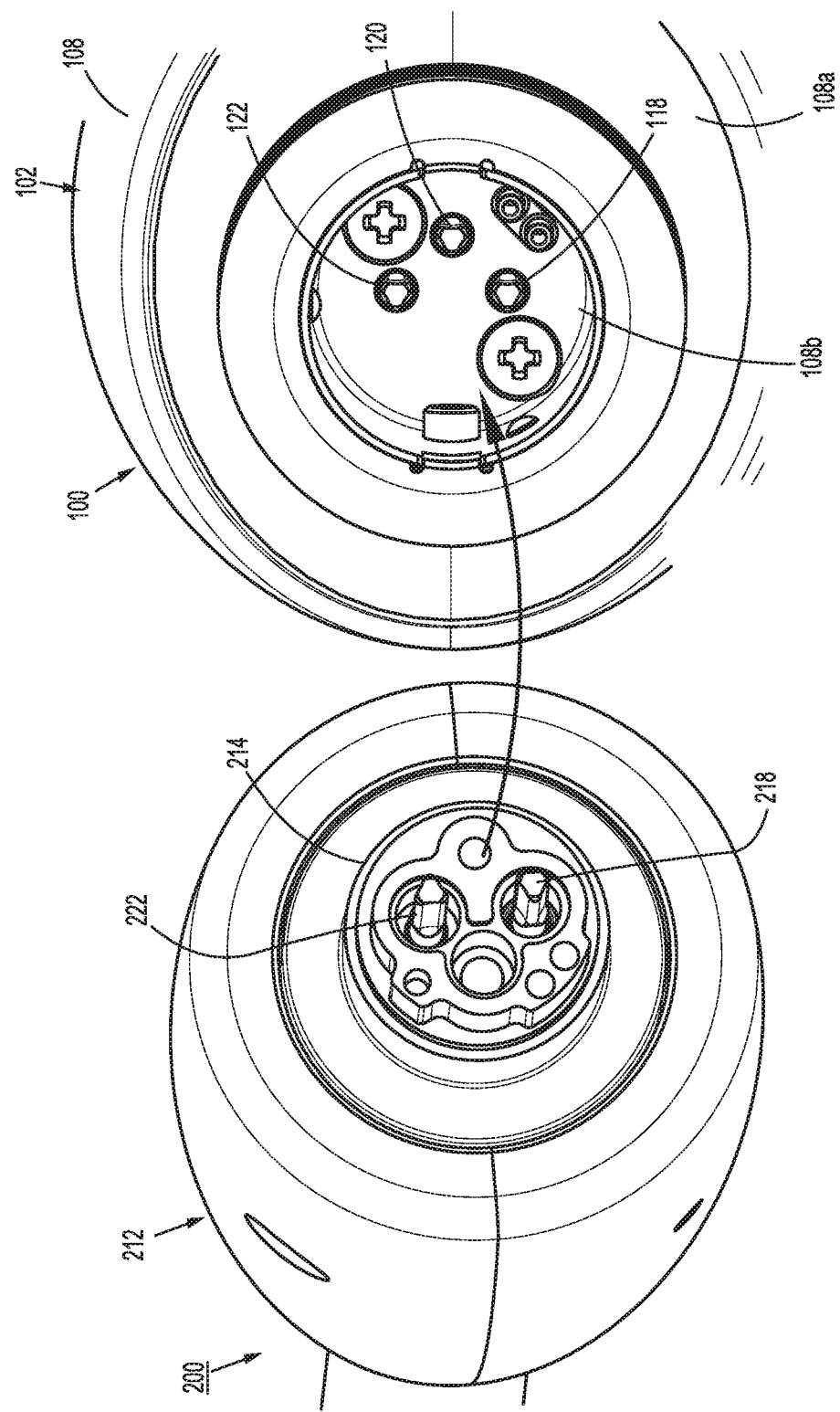
FIG. 3 is a rear, perspective view of a shaft assembly and a powered surgical instrument, of the electromechanical surgical system of FIGS. 1 and 2, illustrating a connection therebetween.

Upper housing portion 108 of handle housing 102 defines a nose or connecting portion 108a configured to accept a corresponding shaft coupling assembly 214 of transmission housing 212 of shaft assembly 200. As seen in FIG. 3, connecting portion 108a of upper housing portion 108 of surgical instrument 100 has a cylindrical recess 108b that receives shaft coupling assembly 214 of transmission housing 212 of shaft assembly 200 when shaft assembly 200 is mated to surgical instrument 100. Connecting portion 108a houses three rotatable drive connectors 118, 120, 122, each independently actuatable and rotatable by the drive mechanism (not shown) housed within handle housing 102.

Upper housing portion 108 of handle housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X" (see FIGS. 1 and 2), relative to handle housing 102; to move an upper jaw or anvil assembly 442 of end effector 400 relative to a lower jaw or cartridge assembly 432 of end effector 400, and/or to fire a stapling and cutting cartridge within cartridge assembly 432 of end effector 400.

In use, as seen in FIG. 3, when shaft assembly 200 is mated to surgical instrument 100, each rotatable drive connector 118, 120, 122 of surgical instrument 100 couples with a corresponding rotatable connector 218, 222 of shaft assembly 200 (a corresponding rotatable connector of shaft assembly 200 for coupling with rotatable drive connector 120 not being shown). In this regard, the interface between corresponding first drive connector 118 and first connector 218, the interface between corresponding second drive connector 120 and second connector (not shown) of shaft assembly 200, and the interface between corresponding third drive connector 122 and third connector 222 are keyed such that rotation of each of drive connectors 118, 120, 122 of surgical instrument 100 causes a corresponding rotation of the corresponding first connector 218, second connector (not shown), and third connector 222 of shaft assembly 200.

Generally, the second drive connector (not shown) of surgical instrument 100 is used to transmit rotation from surgical instrument 100 to shaft assembly 200. It is contemplated that shaft assembly 200 may include a connector for receiving a rotation from second drive connector 120 of surgical instrument 100 for performing the rotation function.

Reference may be made to U.S. Provisional Patent Application Ser. No. 61/669,208, filed on Jul. 9, 2012, or U.S. patent application Ser. No. 13/769,419, filed on Feb. 18, 2013, the entire content of each of which is incorporated herein by reference, for a detailed discussion of the construction, operation and use of the second connector and a second drive train of shaft assembly 200.

It is contemplated that the operation of the drive connector 120 can be blocked by a computer program that is provided in one or more memory devices included in the controller of the instrument 100. Alternatively, drive connector 120 can rotate freely.

The mating of drive connectors 118, 120, 122 of surgical instrument 100 with connectors 218, 222 (and the second drive connector, not shown) of shaft assembly 200 allows rotational forces to be independently transmitted via each of the respective connector interfaces. The drive connectors 118, 120 122 of surgical instrument 100 are configured to be independently rotated by the drive mechanism. In this regard, a function selection module (not shown) of the drive mechanism selects which drive connector or connectors 118, 120, 122 of surgical instrument 100 is to be driven by an input drive component (not shown) of the drive mechanism. Alternatively, an actuator for each of the drive connectors 118, 120, 122 can be provided on the surgical instrument 100.

Since each of drive connectors 118, 120, 122 of surgical instrument 100 has a keyed and/or substantially non-rotatable interface with respective first connector 218, second connector (not shown) and third connector 222 of shaft assembly 200, when shaft assembly 200 is coupled to surgical instrument 100, rotational force(s) are selectively transferred from the drive mechanism of surgical instrument 100 to shaft assembly 200, and on to end effector 400, as will be discussed in greater detail below.

Figure 10:
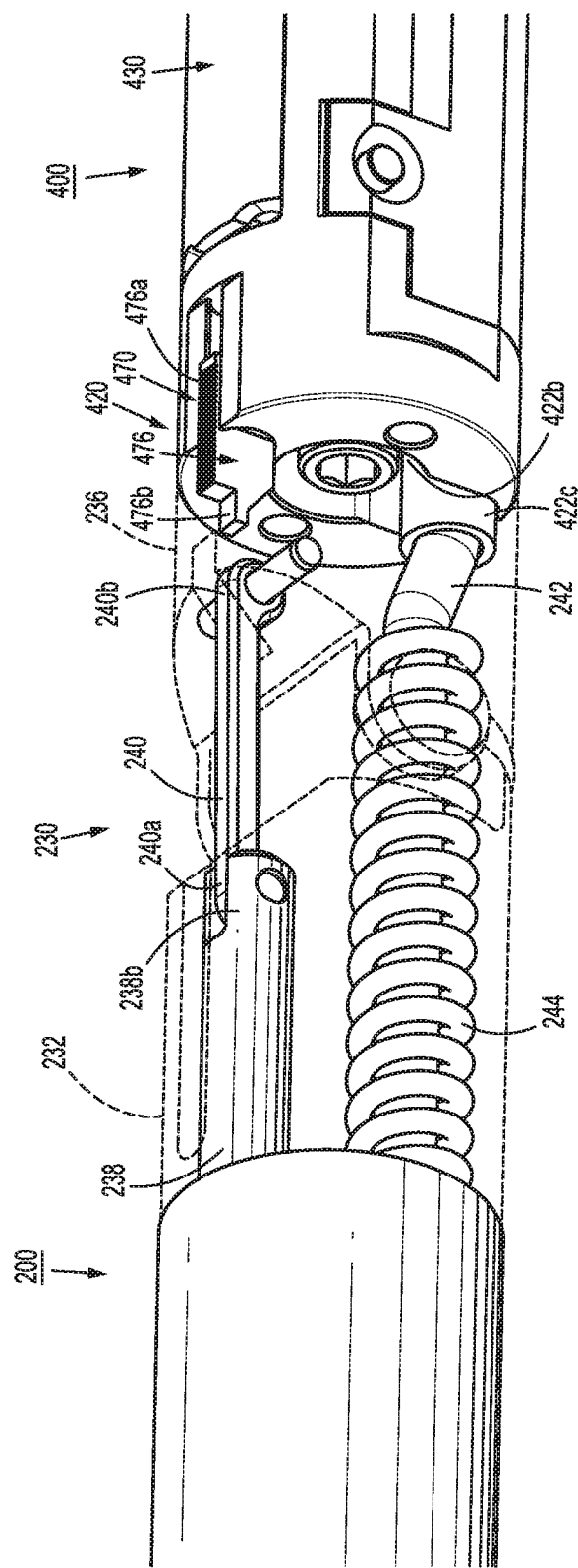
FIG. 10 is an enlarged, perspective view, illustrating the complete connection of the distal end of the shaft assembly with the proximal end of the end effector.

The selective rotation of drive connector(s) 118, 120 and/or 122 of surgical instrument 100 allows surgical instrument 100 to selectively actuate different functions of end effector 400. As will be discussed in greater detail below, selective and independent rotation of first drive connector 118 of surgical instrument 100 corresponds to the selective and independent opening and closing of end effector 400, and driving of a stapling/cutting component of end effector 400. The selective and independent rotation of second drive connector 120 of surgical device 100 corresponds to the selective and independent articulation of tool assembly 304 of end effector 300 transverse to longitudinal axis "X" (see FIG. 4). Additionally, the selective and independent rotation of third drive connector 122 of surgical instrument 100 corresponds to the selective and independent rotation of end effector 400 about longitudinal axis "X" (see FIG. 10) relative to handle housing 102 of surgical instrument 100. In any of the embodiments described herein, the opening and closing of the end effector 400 and the driving of the stapling and/or cutting component of the end effector 400 can be separately driven by two separate drive shafts and drive connectors.

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive connectors 118, 120, 122 of surgical instrument 100, at a given time. In any of the embodiments described herein, more than one motor can be provided in the surgical instrument 100 to, for example separately drive the drive shafts and drive connectors.

Figure 2:
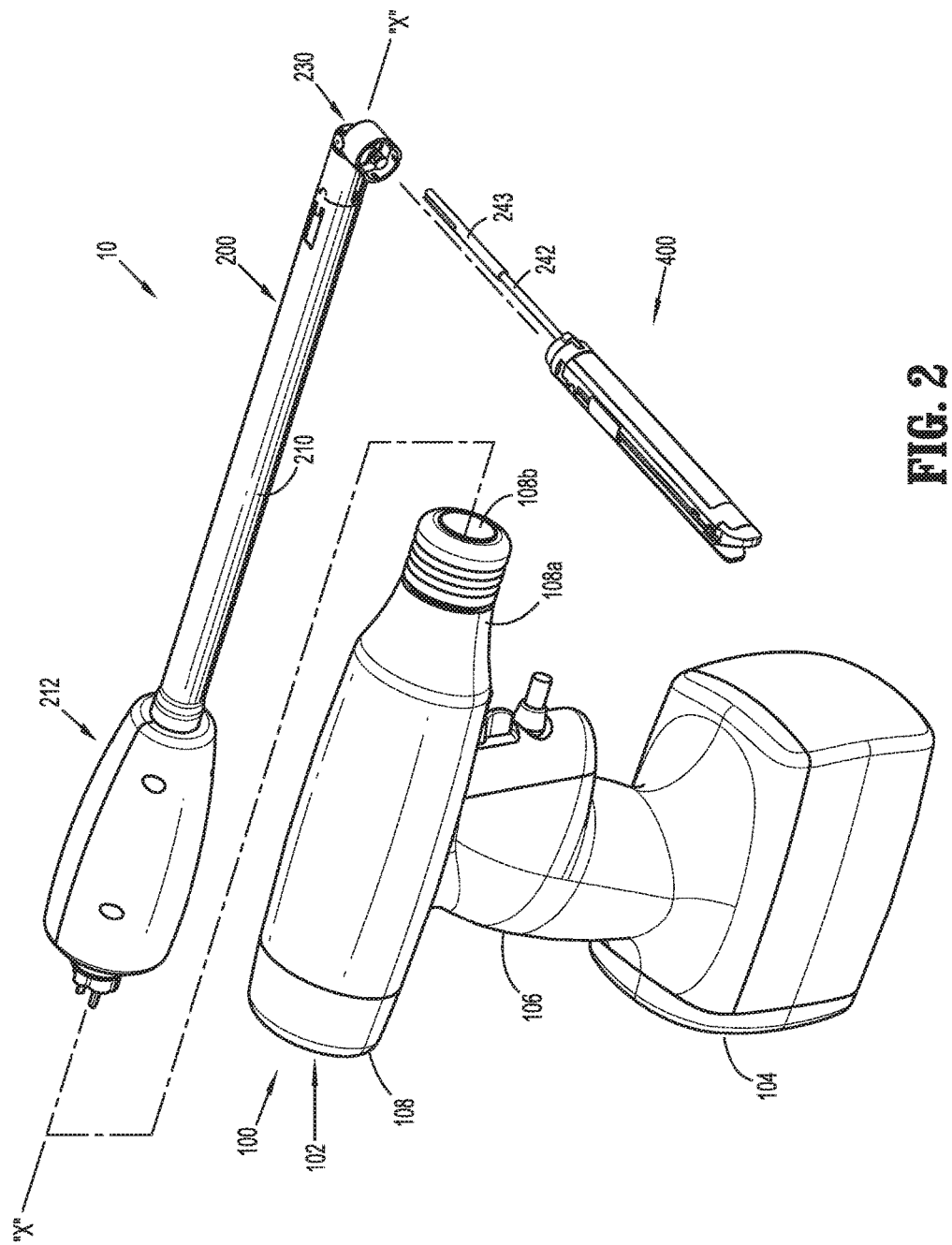
FIG. 2 is a perspective view, with parts separated, of the electromechanical surgical system of FIG. 1.
Figure 2A:
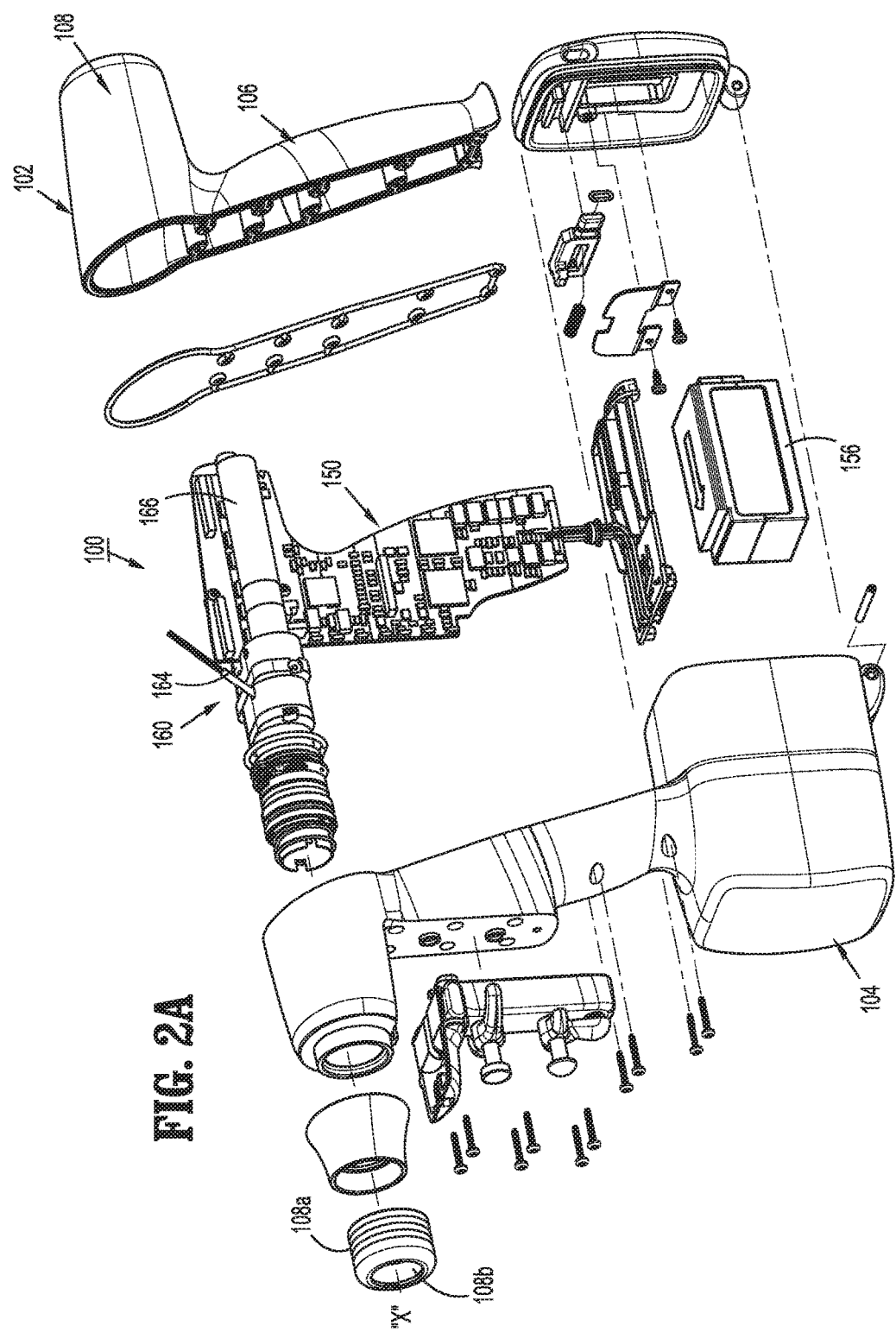
FIG. 2A is a perspective view, with parts separated, of a powered surgical instrument of the electromechanical surgical system of the present disclosure.

As illustrated in FIGS. 1 and 2, handle housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator.

Turning now to FIGS. 1-10, shaft assembly 200 will be shown in detail and described. Shaft assembly 200 is configured to communicate the rotational forces of first, second and third rotatable drive connectors 118, 120 and 122 of surgical instrument 100 to end effector 400. As mentioned above, shaft assembly 200 is configured for selective connection to surgical instrument 100.

As seen in FIGS. 1-10, shaft assembly 200 includes an elongate, substantially rigid, tubular body 210 having a proximal end 210a and a distal end 210b; a transmission housing 212 connected to proximal end 210a of tubular body 210 and being configured for selective connection to surgical instrument 100; and an articulating neck assembly 230 connected to distal end 210b of elongate body portion 210.

Transmission housing 212 is configured to house a pair of gear train systems therein for varying a speed/force of rotation (e.g., increase or decrease) of first and/or second rotatable drive connectors 118 and/or 122 of surgical instrument 100 before transmission of such rotational speed/force to end effector 400.

Transmission housing 212 of shaft assembly 200 is configured and adapted to connect to connecting portion 108a of upper housing portion 108 of surgical instrument 100. As seen in FIGS. 2 and 3, transmission housing 212 of shaft assembly 200 includes a shaft coupling assembly 214 supported at a proximal end thereof.

Shaft assembly 200 may include a first gear train system and a second gear train system, each disposed within transmission housing 212 and tubular body 210. Each gear train system is configured and adapted to vary a speed/force of rotation (e.g., increase or decrease) of first rotatable drive connector 118 of surgical instrument 100 before transmission of such rotational speed/force to end effector 400.

In accordance with an embodiment of the present disclosure, shaft assembly 200, including the first gear system, functions to transmit operative forces from surgical instrument 100 to end effector 400 in order to operate, actuate and/or fire end effector 400. Additionally, in accordance with an embodiment of the present disclosure, shaft assembly 200, including the second gear system, functions to transmit operative forces from surgical instrument 100 to end effector 400 in order rotate shaft assembly 200 and/or end effector 400 relative to surgical instrument 100.

Figure 4:
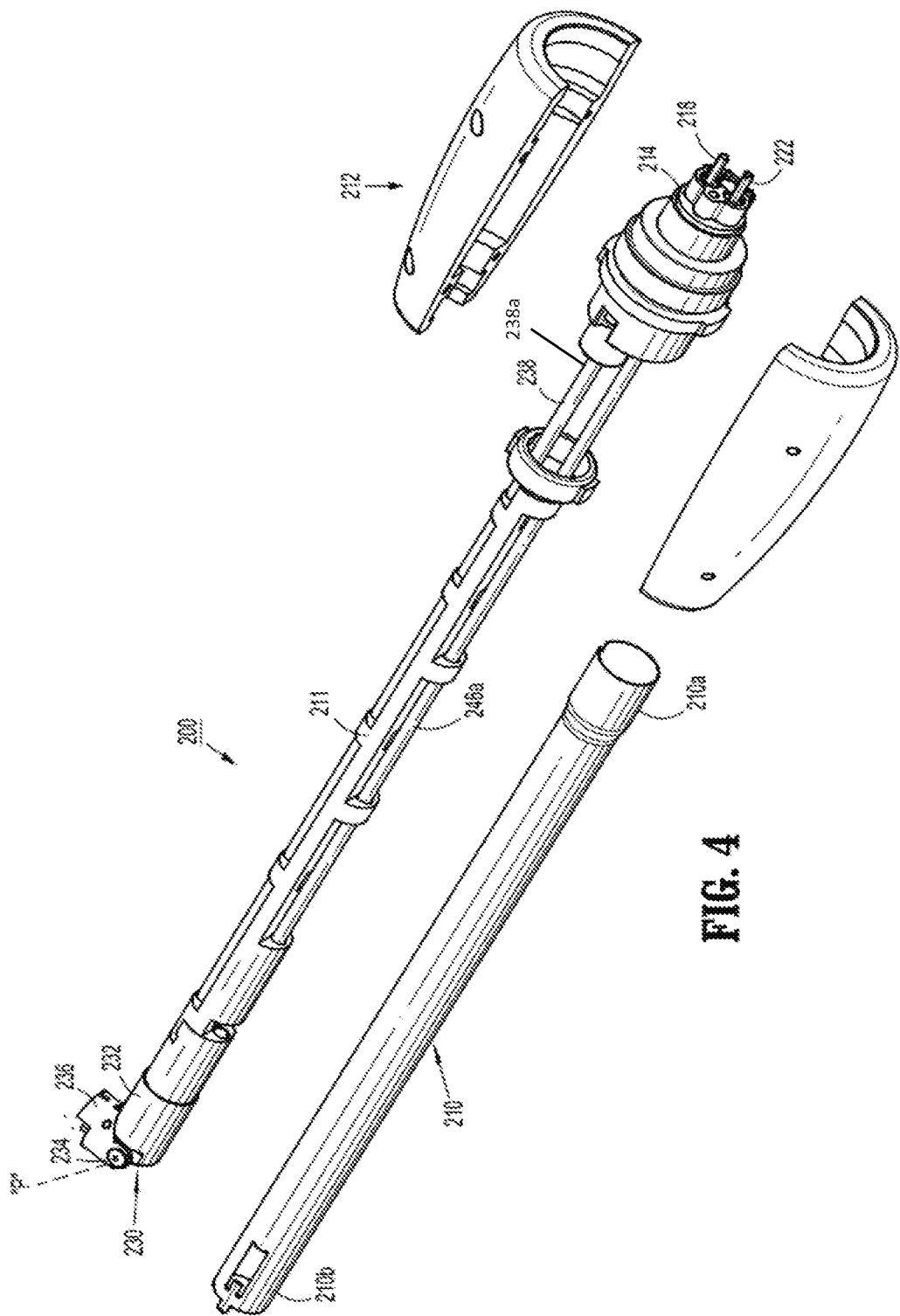
FIG. 4 is a perspective view, with parts separated, of the shaft assembly of FIGS. 1-3.
Figure 5:
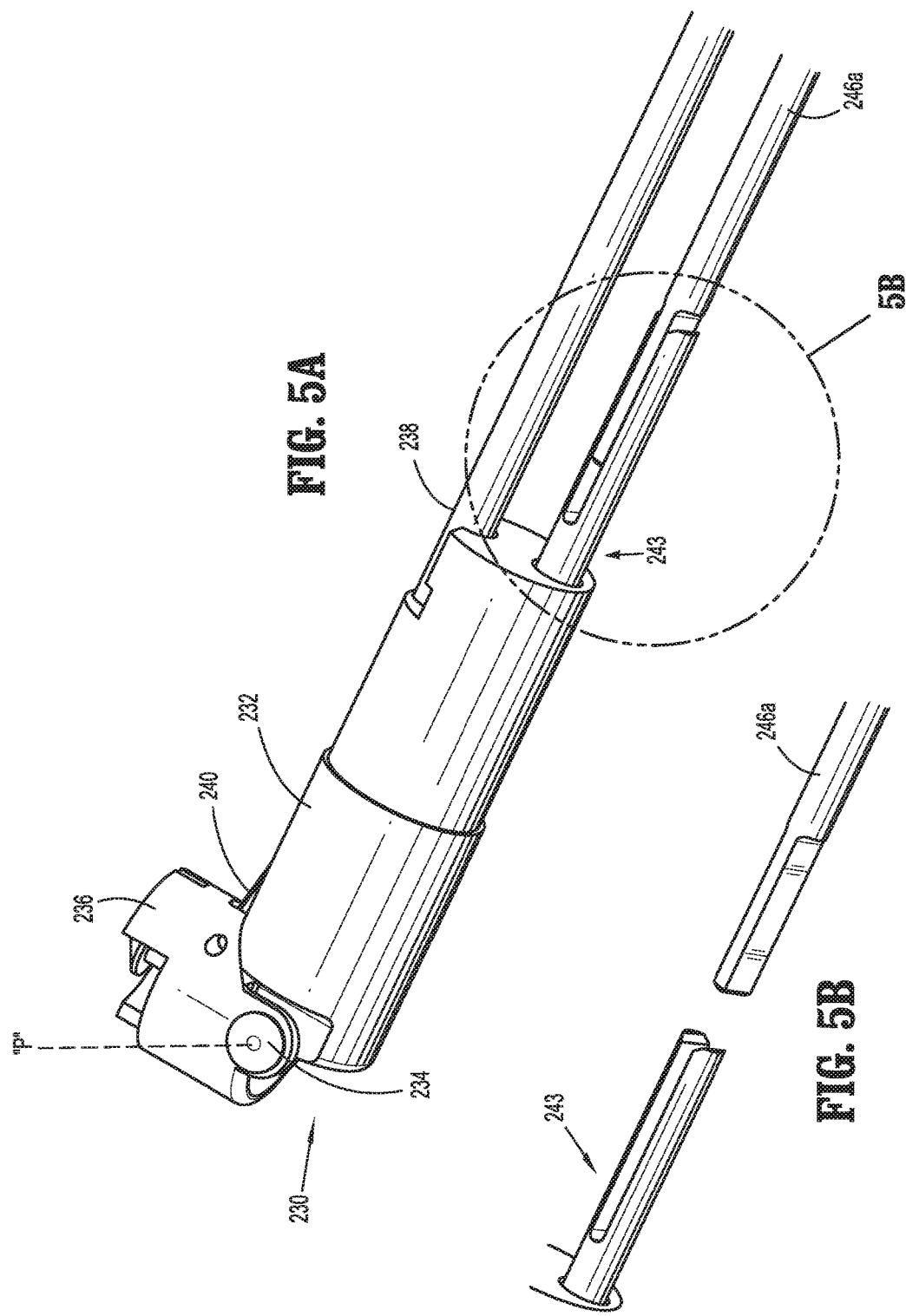
FIG. 5A is a perspective view, with parts separated, of a distal end of the shaft assembly of FIGS. 1-4, with an outer tube removed therefrom.
FIG. 5B is an enlarged view, with parts separated, of the indicated area of detail of FIG. 5A.
Figure 6:
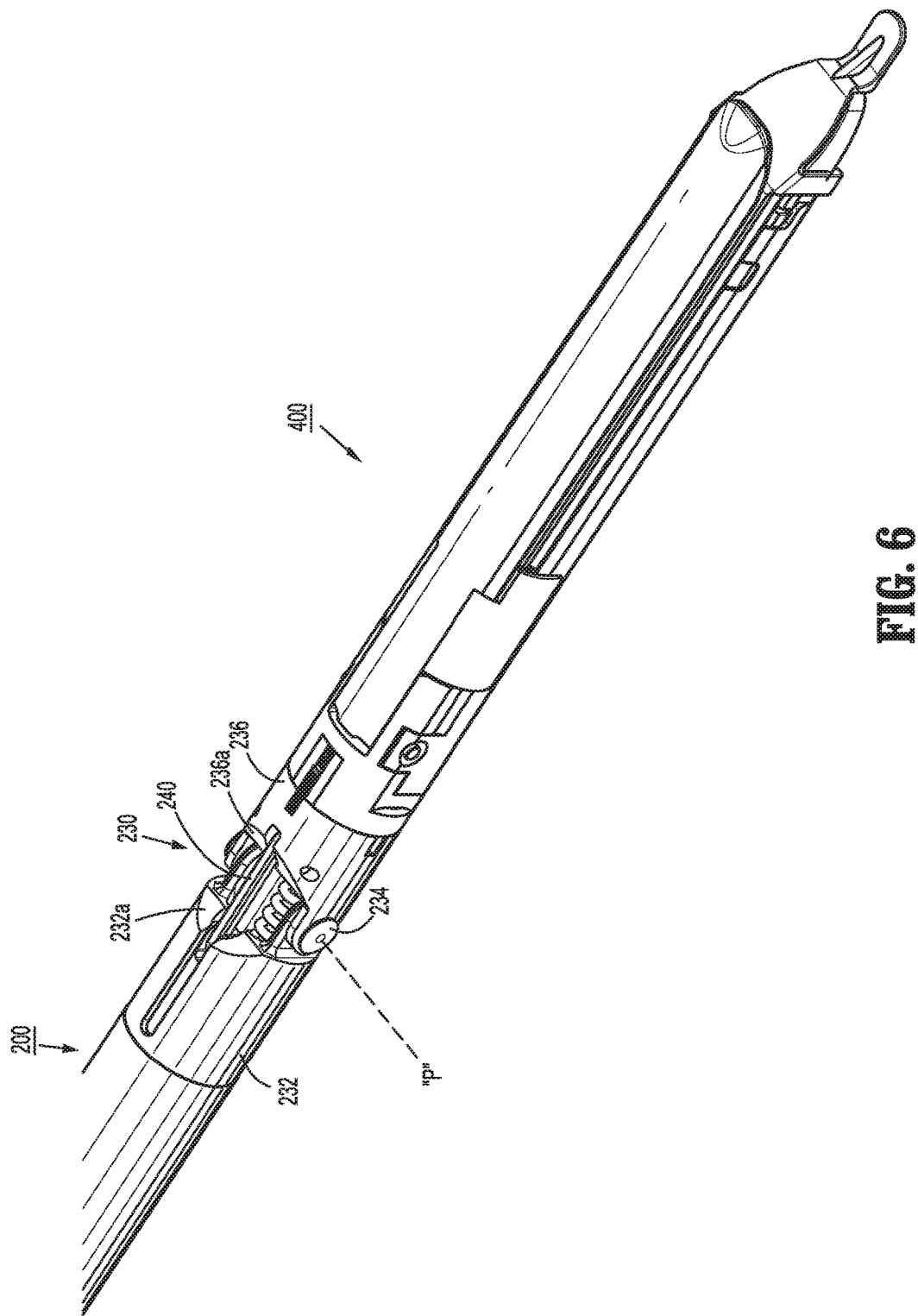
FIG. 6 is a perspective view illustrating an end effector connected to a distal end of the shaft assembly of FIGS. 1-5, oriented in a linear, non-articulated condition.

As seen in FIG. 4, elongate body portion 210 of shaft assembly 200 includes a support frame 211 defining at least two longitudinally extending channels through body portion 210. The channels are configured and dimensioned to rotatably receive and support at least a first output drive shaft or bar 238 (i.e., an articulation bar) of the first gear system, and a second output drive shaft or bar 246a. Each of first output drive shaft or bar 238, and second output drive shaft or bar 246a are elongate and sufficiently rigid to transmit axial or rotational forces from transmission housing 212 to articulating neck assembly 230.

Turning now to FIGS. 4-10, articulating neck assembly 230 is shown and described. Articulating neck assembly 230 includes a proximal neck housing 232; and a distal neck housing 236 pivotally connected to and extending distally from proximal neck housing 232 by a pivot pin 234. Pivot pin 234 defines a pivot axis "P" (see FIG. 6) that is oriented orthogonal to the longitudinal axis "X" and extends through the longitudinal axis "X".

Articulation neck assembly 230 receives a distal end of output drive shaft or articulation bar 238. Articulation bar 238 may include a threaded proximal end 238a that is in threaded engagement with a distal end of an internally threaded nut (not shown). The threaded nut may be rotatably supported and axially fixed within a pocket (not shown) formed in transmission housing 212. A proximal end of the threaded nut is keyed to a distal end of first rotatable connector 218 of shaft assembly 200.

Articulation bar 238 includes a distal end 238b pivotally connected to a proximal end 240a of an articulation link 240. A distal end 240b of articulation link 240 is pivotally connected to distal neck housing 236.

Figure 21:
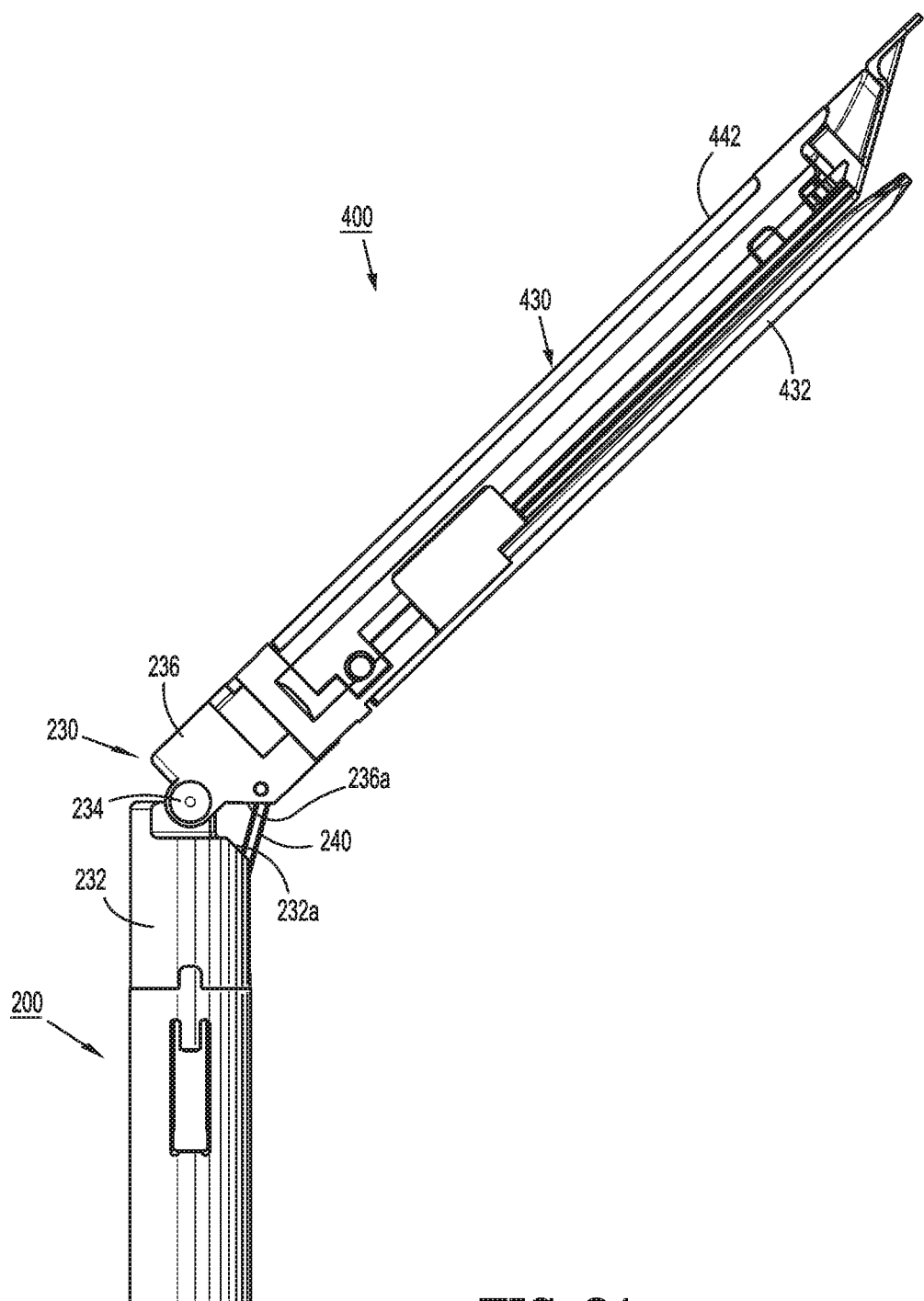
FIG. 21 is a top, plan view of the distal end of the shaft assembly and the end effector, shown in a partially articulated condition.
Figure 22:
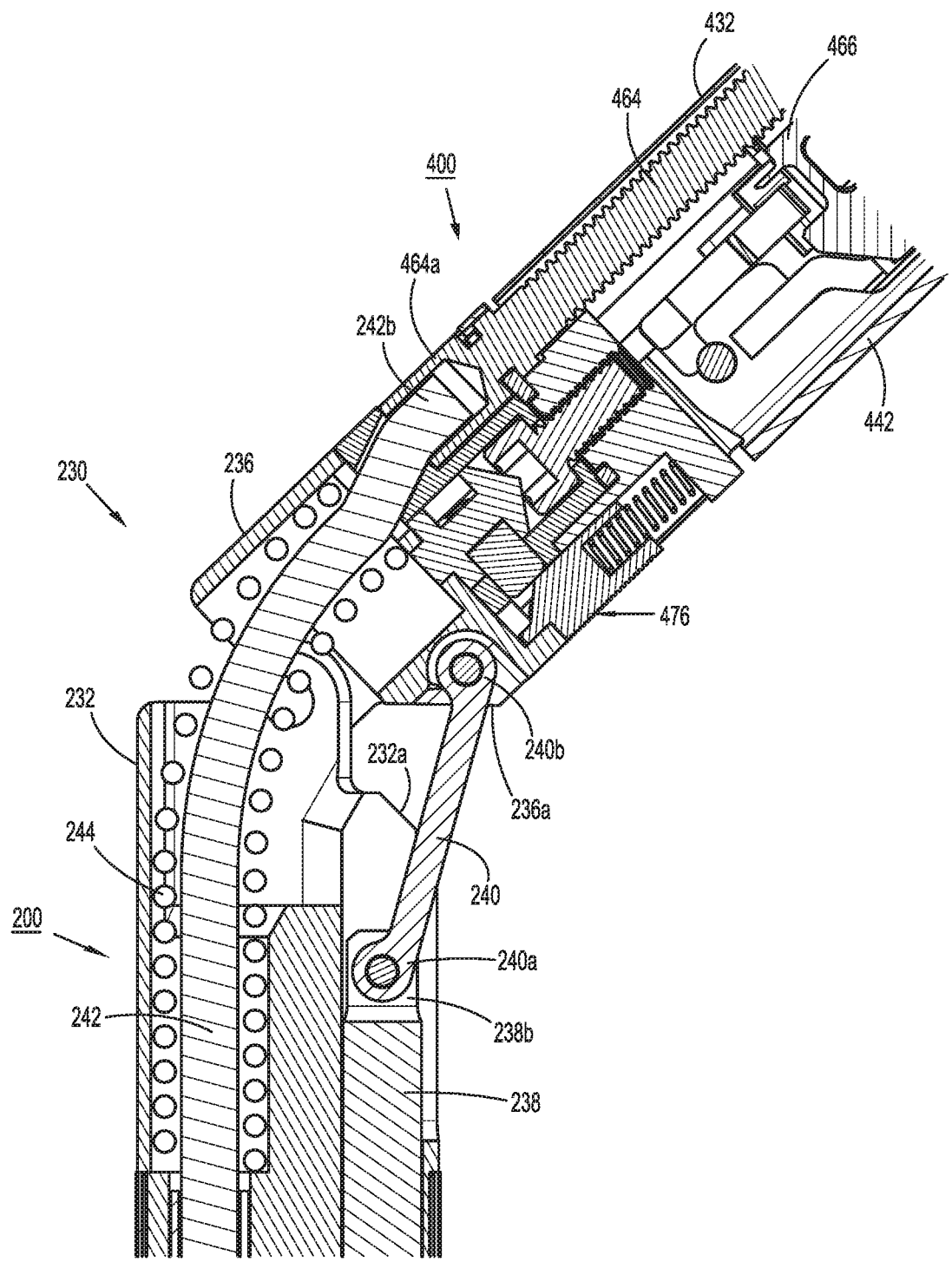
FIG. 22 is a cross-section view of the partially articulated end effector of FIG. 21.
Figure 23:
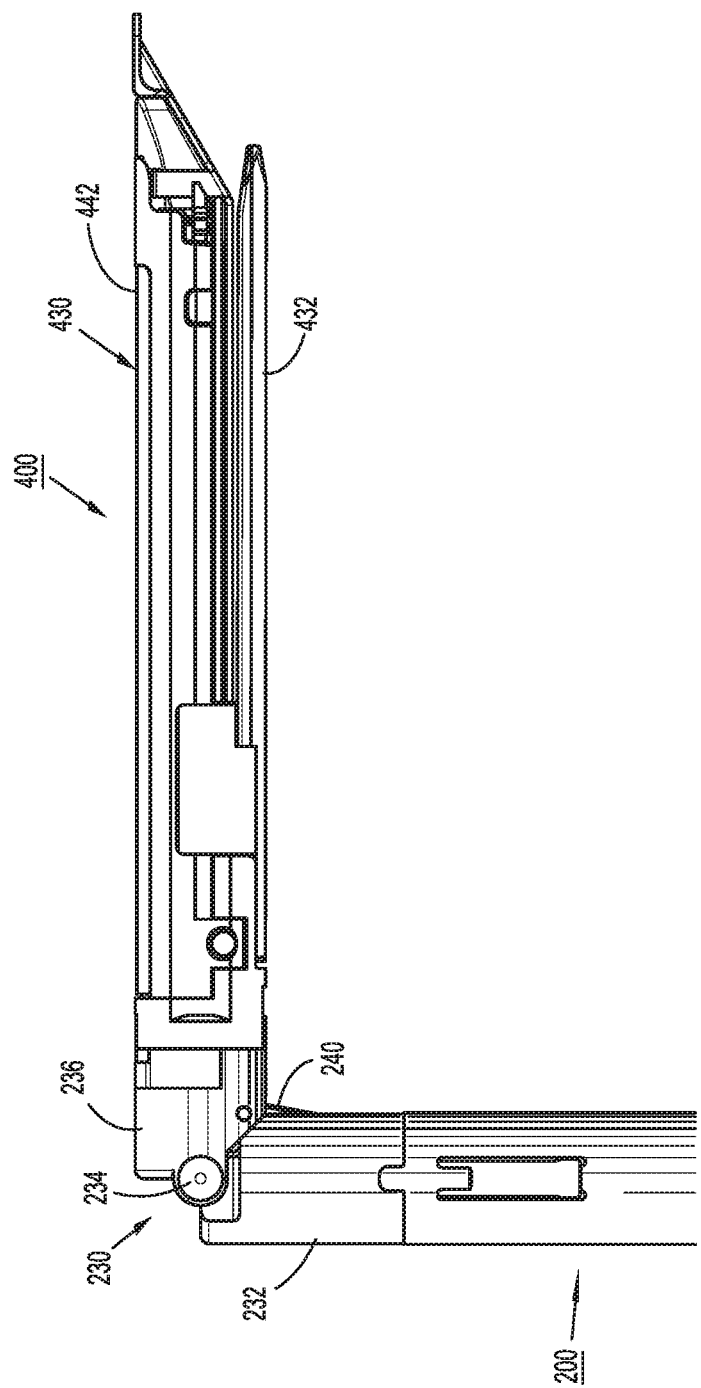
FIG. 23 is a top, plan view of the distal end of the shaft assembly and the end effector, shown in a fully articulated condition.
Figure 24:
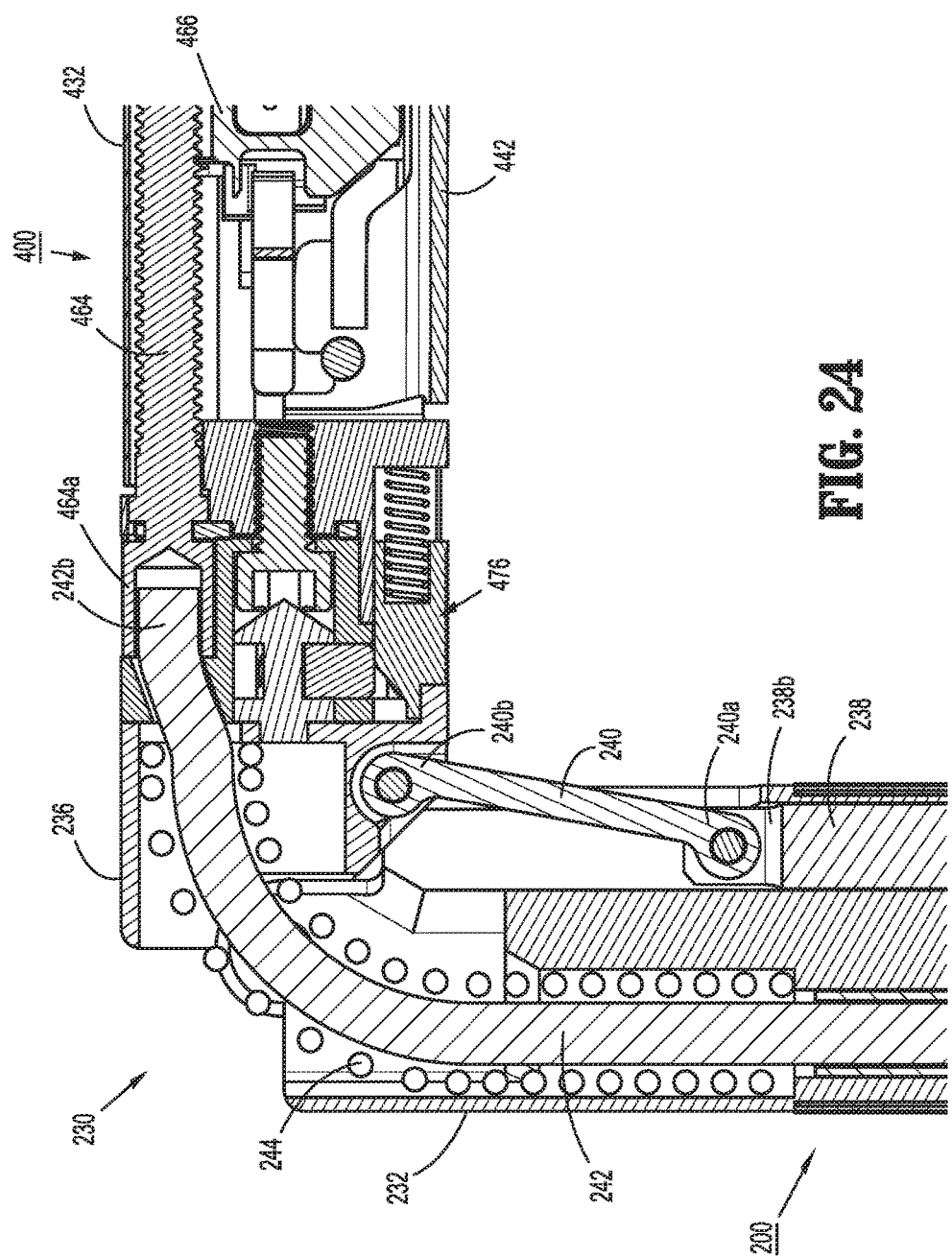
FIG. 24 is a cross-section view of the fully articulated end effector of FIG. 23.

Proximal neck housing 232 defines a chamfered distal surface 232a, and distal neck housing 236 defines a chamfered proximal surface 236a. In an embodiment, chamfered surfaces 232a, 236a are in juxtaposed relation to one another. In use, when end effector 400 is actuated to an off-axis orientation, as will be discussed in greater detail below, chamfered surfaces 232a, 236a of proximal neck housing 232 and distal neck housing 236 are approximated toward one another. Desirably, each chamfered surface 232a, 236a is angled at about 45° relative to the longitudinal axis "X". Specifically, chamfered surface 232a of proximal neck housing 232 is angled at about (−)45° relative to the longitudinal axis "X", while chamfered surface 236a of distal neck housing 236 is angled at about (+)45° relative to the longitudinal axis "X". In this manner, when proximal neck housing 232 and distal neck housing 236 are actuated from a linear non-actuated orientation to a maximum off-axis orientation, as seen in FIGS. 23 and 24, end effector 400 is oriented at about 90° relative to the longitudinal axis "X". In use, end effector 400 may be oriented at any angular orientation from about 0° to about 90° relative to the longitudinal axis "X", as needed or desired, such as, for example, about 45°, as seen in FIGS. 21 and 22.

In accordance with the present disclosure, distal neck housing 236 is pivotable in a single direction relative to proximal neck housing 232.

As seen in FIGS. 7-20, articulating neck assembly 230 further includes a distal connection hub 250 rotatably supported and/or coupled in a distal end of distal neck housing 236. Connection hub 250 supports a coupling lug 250a projecting distally therefrom along a centerline of connection hub 250. Coupling lug 250a includes a head 250b defining an angled distal surface 250c, in the form of a cone or the like, and an annular race or groove 250d defined in an outer annular surface thereof.

Shaft assembly 200 is configured to accommodate a flexible drive cable 242 and a cable coupler 243 extending from end effector 400, as will be described in greater detail below.

Shaft assembly 200 includes a reinforcing coil spring 244 configured to accommodate and surround flexible drive cable 242 of end effector 400, when end effector 400 is connected to shaft assembly 200. In accordance with the present disclosure, reinforcing coil spring 244 is constrained at a proximal end and a distal end thereof, and is installed under compression. Reinforcing coil spring 244 functions to help keep flexible drive cable 242 from kinking during articulation of end effector 400. Reinforcing coil spring 244 also functions to help keep flexible drive cable 242 from failing due to unwinding and/or "pig tailing" during rotation thereof.

Figure 7:
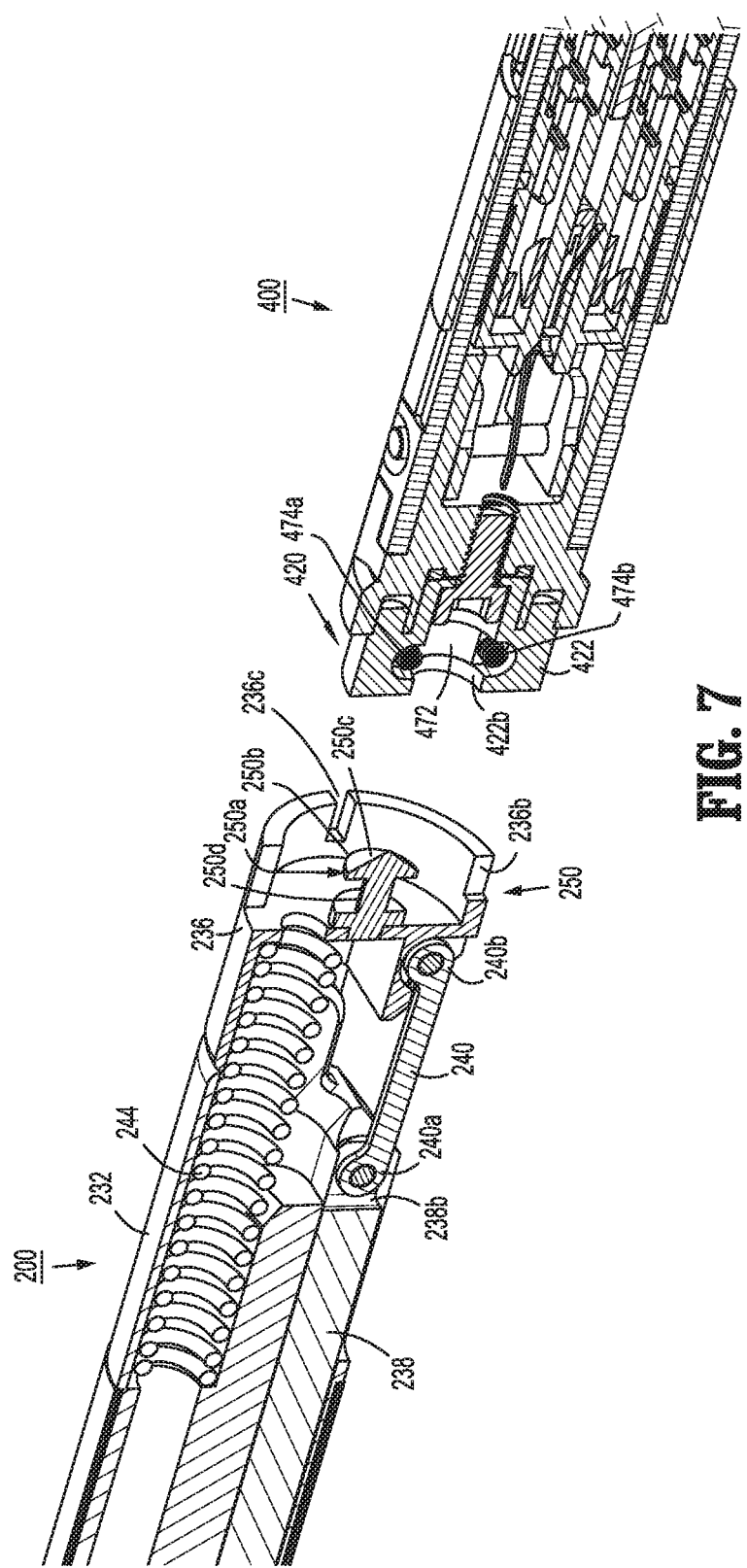
FIG. 7 is an enlarged, longitudinal, cross-sectional view, with parts separated, of the distal end of the shaft assembly operatively axially aligned with a proximal end of the end effector, and with the end effector rotated 90° relative to the shaft assembly.
Figure 8:
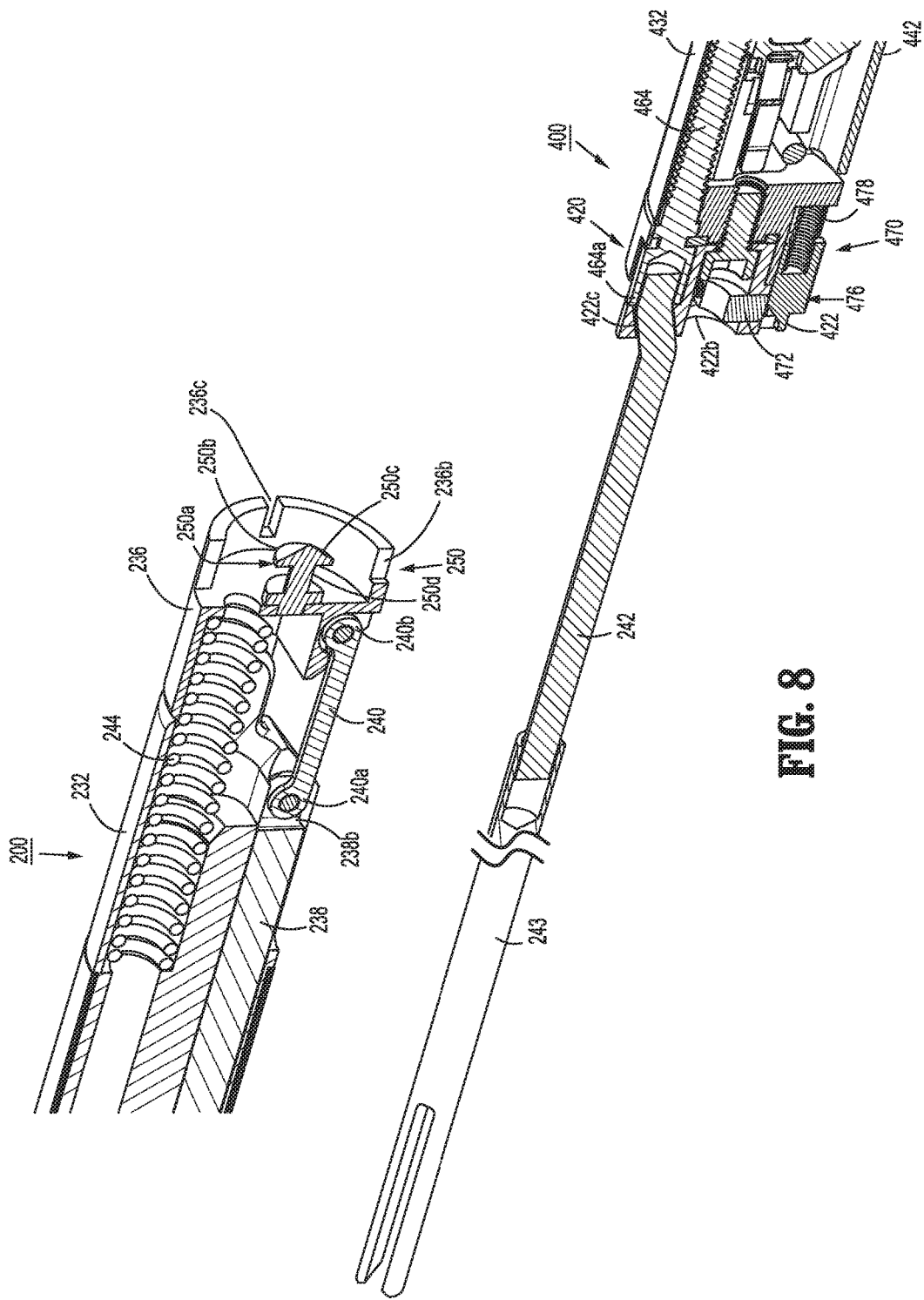
FIG. 8 is an enlarged, longitudinal, cross-sectional view, with parts separated, of the distal end of the shaft assembly operatively aligned with a proximal end of the end effector.
Figure 9:
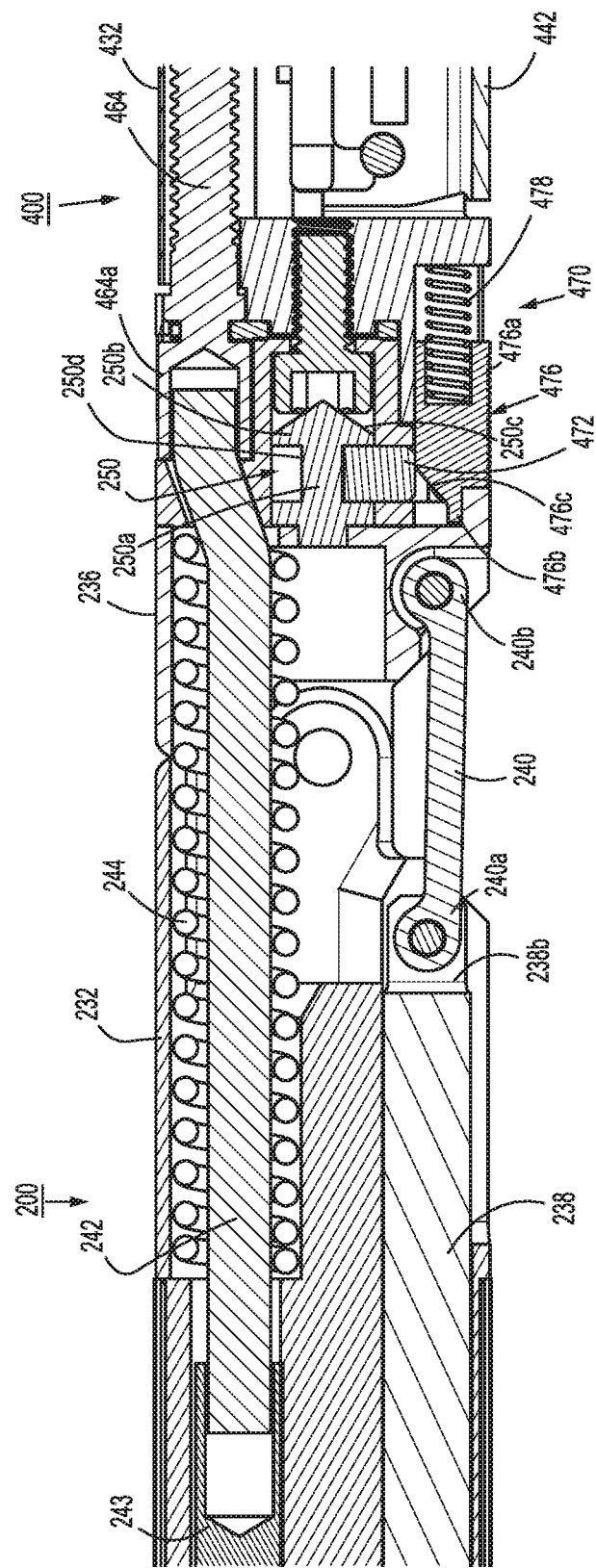
FIG. 9 is an enlarged, elevational view, illustrating a complete connection of the distal end of the shaft assembly with the proximal end of the end effector.
Figure 12:
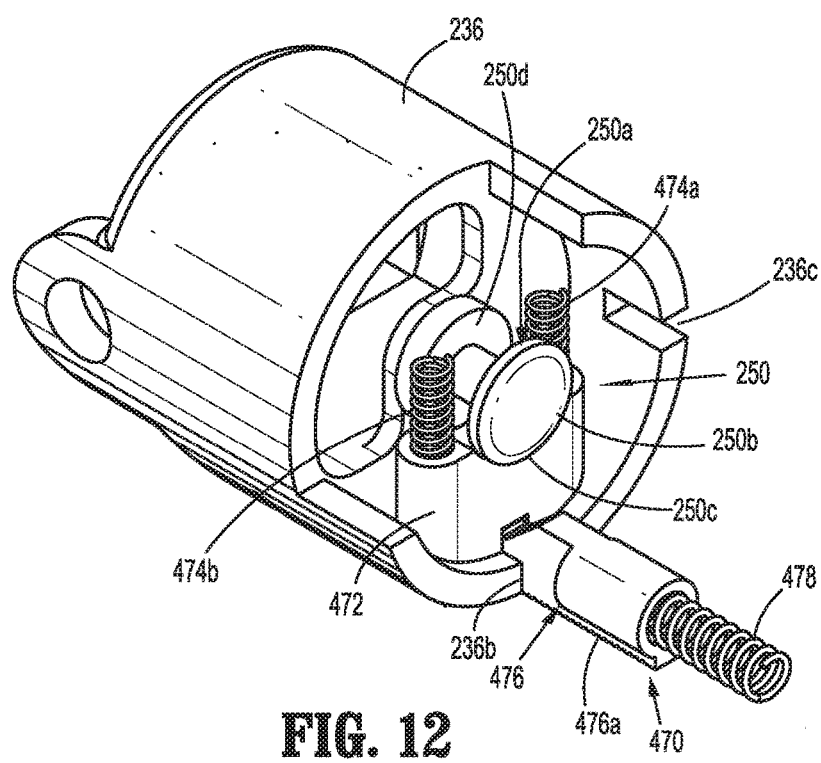
FIG. 12 is a schematic, perspective view of a distal neck portion of the shaft assembly, with the lock mechanism in the unlocked position.
Figure 13:
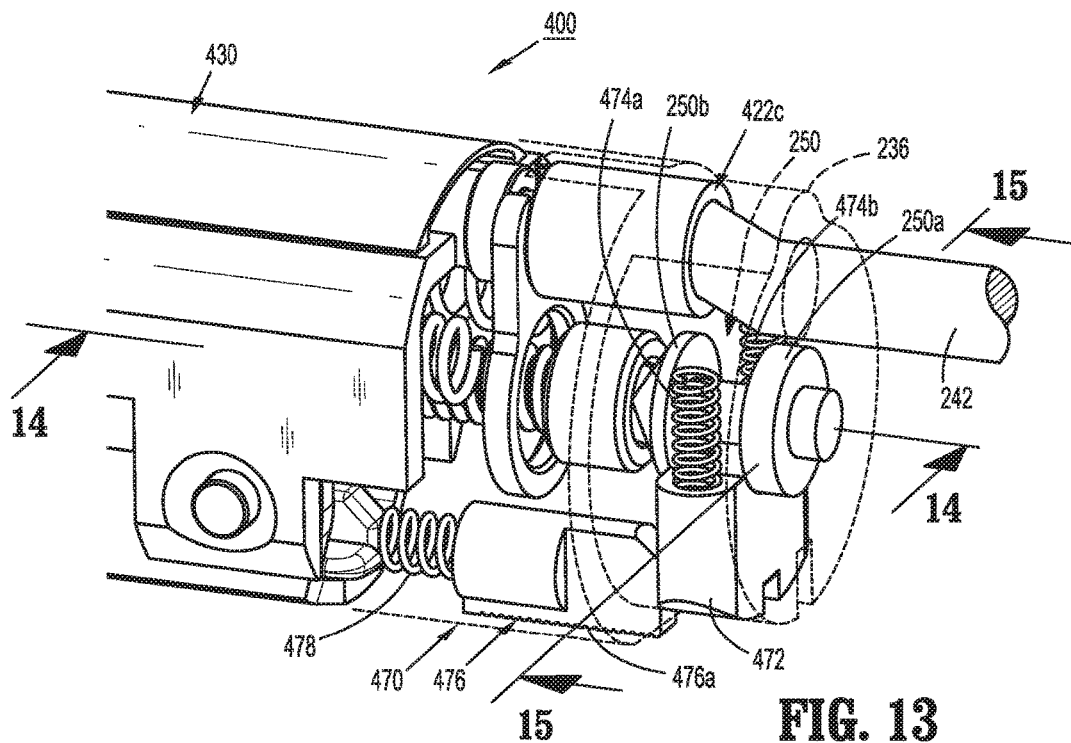
FIG. 13 is a perspective view, illustrating the shaft assembly connected to the end effector while the lock mechanism is in the locked condition.

As seen in FIGS. 7, 8 and 12, distal neck housing 236 defines a first annular notch 236b extending distally therefrom, and a second annular notch 236c extending distally therefrom, wherein the first annular notch 236b and the second annular notch 236c are disposed at approximately 90° relative to one another. It is contemplated that any number of notches may be provided and may be disposed ay any desired angle relative to one another.

In accordance with the present disclosure, as seen in FIGS. 5A and 5B, cable coupler 243 of flexible drive cable 242 of end effector 400 is configured for selective connection to a distal end of first output drive shaft 246a of the first gear system of shaft assembly 200. It is contemplated that cable coupler 243 is configured for non-rotatable connection to first output drive shaft 246a or second output drive shaft 258a. In accordance with the present disclosure, since flexible drive cable 242, including cable coupler 243, form a part of end effector 400, each time a new end effector 400 is coupled to shaft assembly 200 a new flexible drive cable 242 (and cable coupler 243) is also loaded into of coupled to shaft assembly 200.

In accordance with the present disclosure, when end effector 400 is connected to shaft assembly 200, cable coupler 243 is located proximally of proximal neck housing 232 with flexible drive cable 242 extending from and between proximal neck housing 232 and distal neck housing 236. In order to properly load or connect end effector 400 (including flexible drive cable 242 and cable coupler 243) to shaft assembly 200, in accordance with the present disclosure, proximal neck housing 232 and distal neck housing 236 must be in the non-articulated position relative to one another. With proximal neck housing 232 and distal neck housing 236 in the non-articulate position relative to one another, flexible drive cable 242 (and cable coupler 243) may be threaded or fed into or withdrawn from shaft assembly 200.

Turning now to FIGS. 7-20, a detailed discussion of the construction and operation of end effector 400 is provided. End effector 400 is constructed substantially in accordance with end effector 400 disclosed in U.S. Provisional Patent Application Ser. No. 61/659,116, filed on Jun. 13, 2012, entitled "Apparatus for Endoscopic Procedures", the entire content of which being incorporated herein by reference, and thus will only be discussed in detail herein to the extent necessary to describe differences in construction and operation thereof. End effector 400 may be configured and adapted to apply a plurality of linear rows of fasteners, which in embodiments may be of various sizes, and which, in certain embodiments may have various lengths or rows, e.g., about 30, 45 and 60 mm in length.

Figure 11:
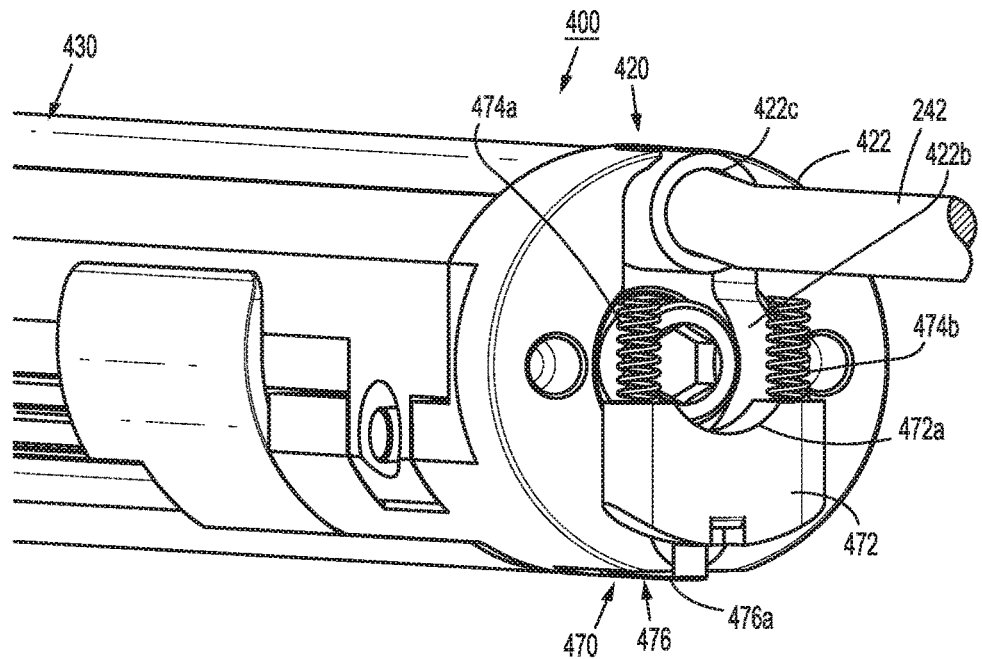
FIG. 11 is a rear perspective view of the end effector illustrating a lock mechanism thereof in an unlocked condition.

As seen in FIGS. 7, 8 and 11, end effector 400 includes a mounting portion 420 having a coupling member 422 configured for selective connection to distal neck housing 236 of shaft assembly 200. End effector 400 further includes a jaw assembly 430 connected to and extending distally from mounting portion 420. As seen in FIGS. 21 and 23, jaw assembly 430 includes a lower jaw 432 pivotally connected to mounting portion 420 and being configured to selectively support a cartridge assembly therein, and an upper jaw 442 secured to mounting portion 420 and being movable, relative to lower jaw 432, between approximated and spaced apart positions.

Coupling member 422 is substantially cylindrical and includes a rear or proximal wall 422a defining a central opening 422b therein, and a passage 422c therein. Central opening 422b is configured and dimensioned to receive head 250b of lug 250a therein. Passage 422c is configured and dimensioned to axially align with or create a pathway to coupling socket 464a of lead or drive screw 464 of end effector 400, as will be discussed in greater detail below. In this manner, when end effector 400 is connected to shaft assembly 200, distal end 242b of flexible drive cable 242 is guided into coupling socket 464a of lead or drive screw 464 of end effector 400 to establish a connection therewith, as will be discussed in greater detail below.

Coupling member 422 of end effector 400 supports a lock mechanism 470 for selectively securing end effector 400 to shaft assembly 200. Lock mechanism 470 includes a lock bar 472 slidably supported in coupling member 422 so as to slide in a plane transverse or orthogonal to central opening 422b. Lock mechanism 470 includes at least one biasing member for biasing lock bar 472 to an unlocked position wherein lock bar 472 does not engage or is not disposed within annular race or groove 250c of lug 250a, as will be discussed in greater detail below. In an embodiment of the present disclosure, lock mechanism 470 includes a pair of biasing members 474a, 474b disposed at opposed ends of lock bar 472 and extending substantially orthogonal to lock bar 472, and being disposed in a plane of movement of lock bar 472. Biasing members 474a, 474b are spaced a distance from one another which is less than a diameter or transverse cross-sectional dimension of head 250b of lug 250a, and/or less that a diameter of central opening 422b of coupling member 422.

Lock bar 472 includes an arcuate or substantially U-shaped surface 472a oriented toward central opening 422b of coupling member 422.

Lock mechanism 470 further includes a lock actuator 476 slidably supported in mounting portion 420 of end effector 400. Lock actuator 476 is in the form of a lock button or slide which is slidable in distal and proximal axial directions. Lock actuator 476 defines a finger engaging surface 476a exposed along an outer surface thereof. Lock actuator 476 includes a finger or nose 476b extending proximally from an angled or ramped proximal surface 476c thereof. Lock mechanism 470 includes a biasing member 478 acting on lock actuator 476 for biasing lock actuator 476 to a proximal position.

Lock actuator is slidable between a distal-most position, a proximal-most position, and an intermediate position upon actuation by an end user, or automatically.

Figure 14:
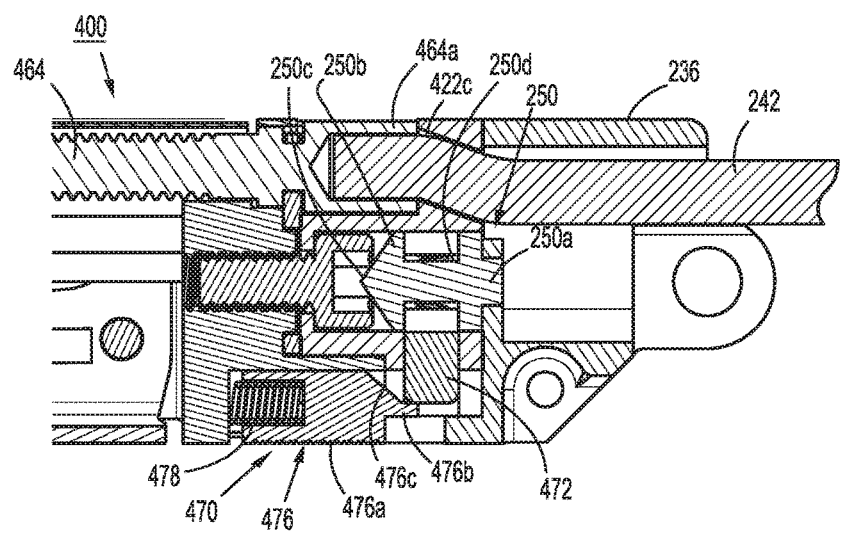
FIG. 14 is a cross-sectional view of the proximal end of the end effector of FIG. 13, as taken through 14-14 of FIG. 13, with the shaft assembly connected thereto and with the lock mechanism in the locked condition.
Figure 15:
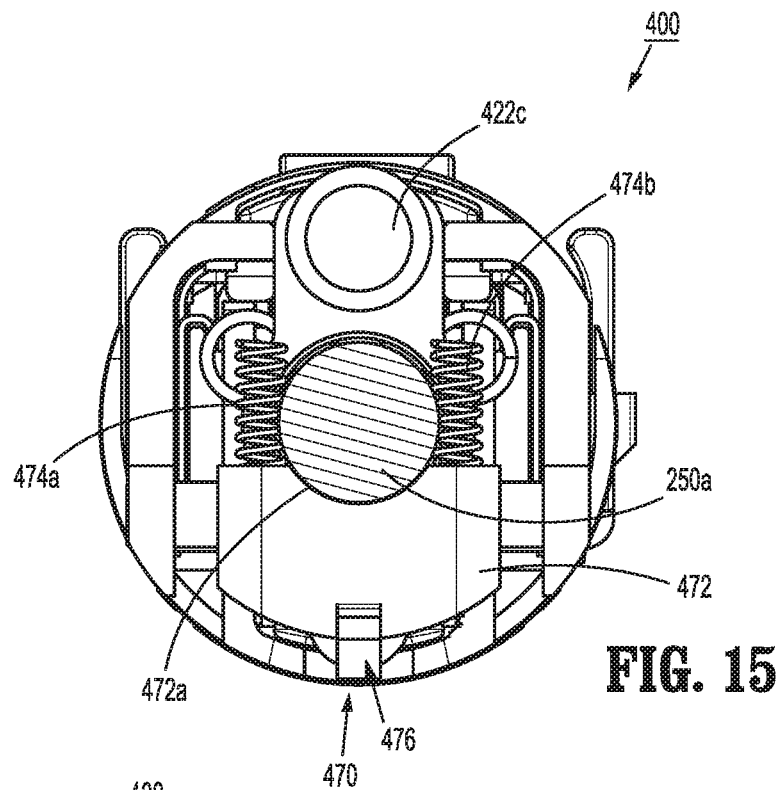
FIG. 15 is a cross-sectional view of the end effector of FIG. 13, as taken through 15-15 of FIG. 13, with the shaft assembly connected thereto and with the lock mechanism in the locked condition.
Figure 16:
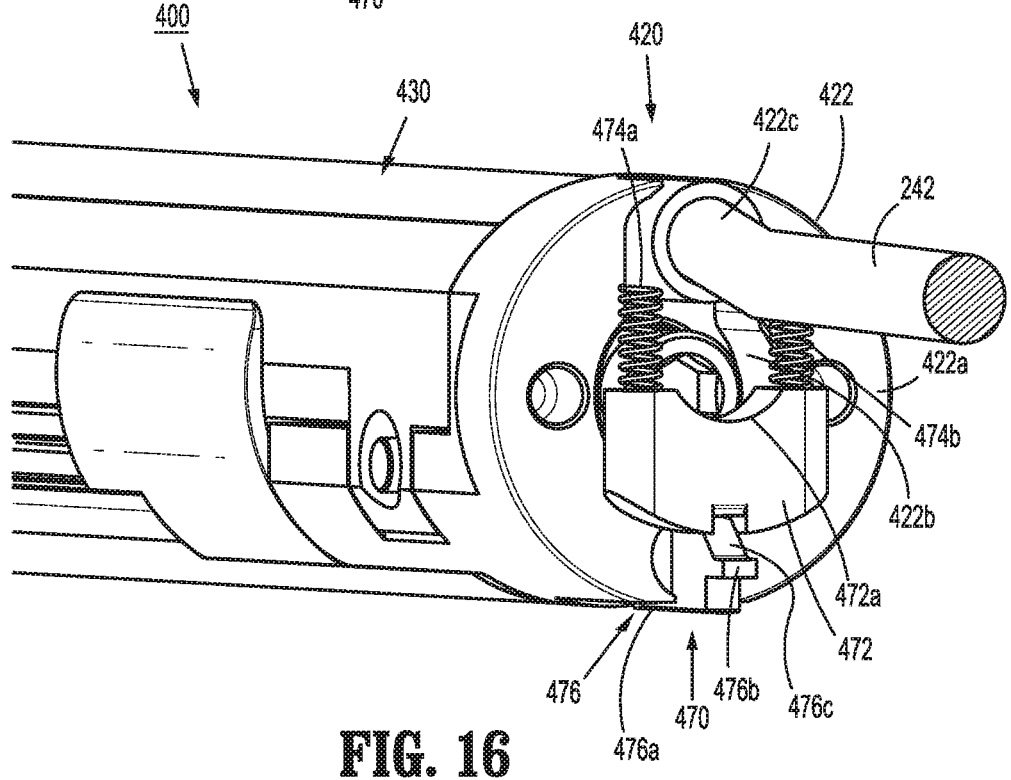
FIG. 16 is a rear perspective view of the end effector illustrating the lock mechanism thereof in a locked condition.
Figure 17:
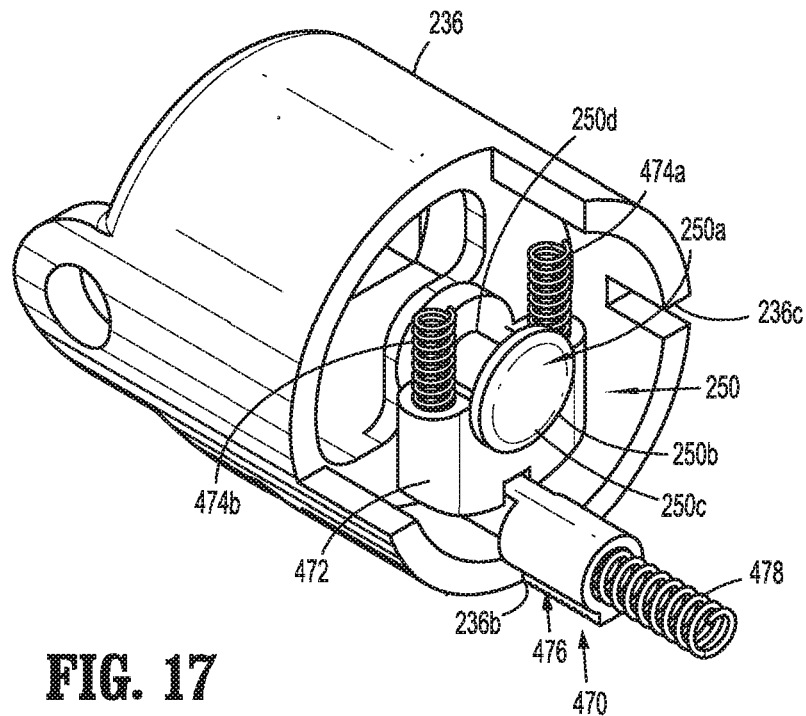
FIG. 17 is a schematic, perspective view of the distal neck portion of the shaft assembly, with the lock mechanism in the locked condition.
Figure 18:
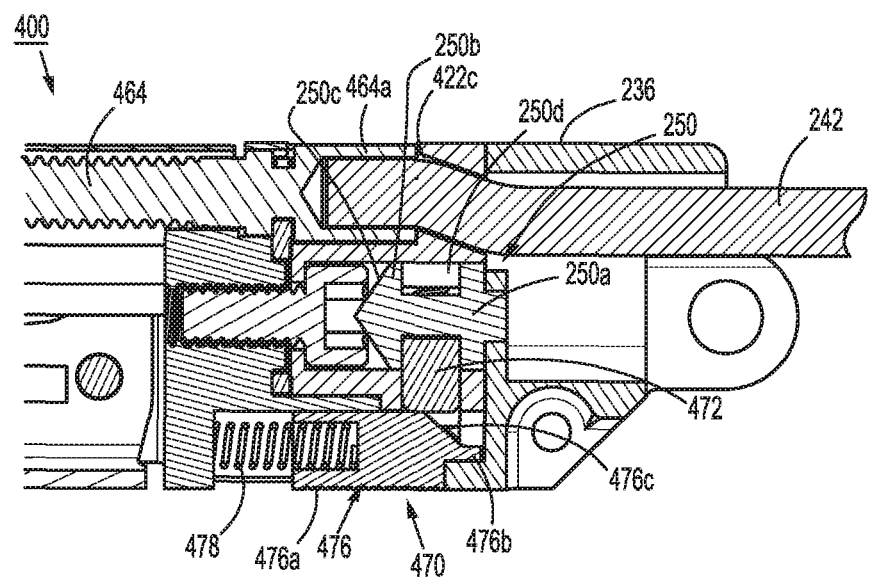
FIG. 18 is a cross-sectional view of the proximal end of the end effector of FIG. 16, as taken through 14-14 of FIG. 13, with the shaft assembly connected thereto and with the lock mechanism in an unlocked condition.

As seen in FIG. 14, lock actuator 476 includes a first or distal-most position wherein biasing member 478 is compressed and/or biased, and wherein lock bar 472 is in an unactuated condition. When lock actuator 476 is in the distal-most position, lock mechanism 470 is in an unlocked condition, wherein lock bar 472 is moved, by biasing member 474a, 474b, away from central opening 422b of coupling member 422, thus clearing central opening 422b for reception of head 250b of lug 250a of shaft assembly 200. In the distal-most position of lock actuator 476, lock bar 472 may rest against nose 476b of lock actuator 476.

As seen in FIGS. 13 and 15-18, lock actuator 476 includes a second or proximal-most position wherein biasing member 478 is substantially uncompressed and/or unbiased, and wherein lock bar 472 is in an actuated condition. When lock actuator 476 is in the proximal-most position, lock mechanism 470 is in a locked condition, wherein lock bar 472 is moved, cammed or urged, by angled or ramped proximal surface 476c of lock actuator 476, toward central opening 422b of coupling member 422, thus at least partially obstructing central opening 422b and entering annular race or groove 250d of lug 250a of shaft assembly 200 (when end effector 400 and shaft assembly 200 are connected to one another). In the proximal-most position of lock actuator 476, lock bar 472 may rest against an inner surface 476d of lock actuator 476 which is located distal of angled or ramped proximal surface 476c of lock actuator 476.

Figure 19:
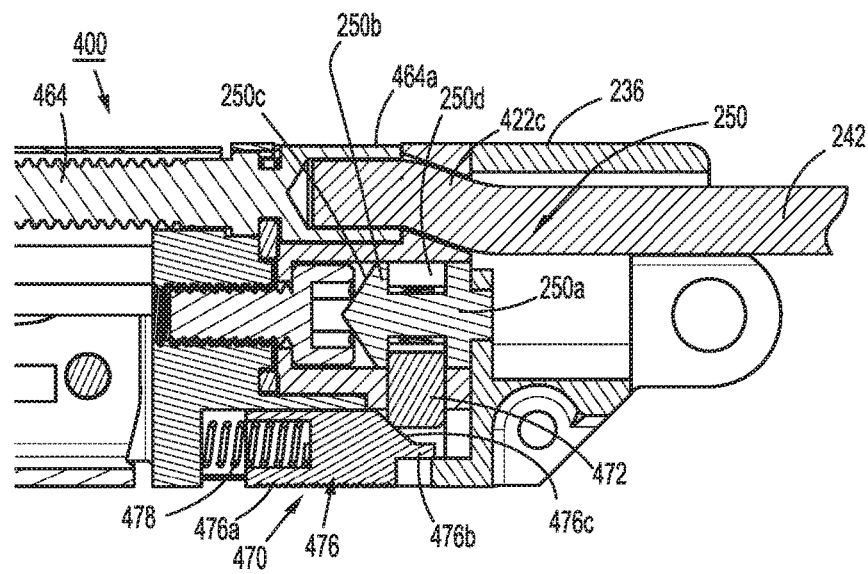
FIG. 19 is a cross-sectional view of the proximal end of the end effector of FIG. 16, as taken through 14-14 of FIG. 13, with the shaft assembly connected thereto and with the lock mechanism in an auto unlocked condition.
Figure 20:
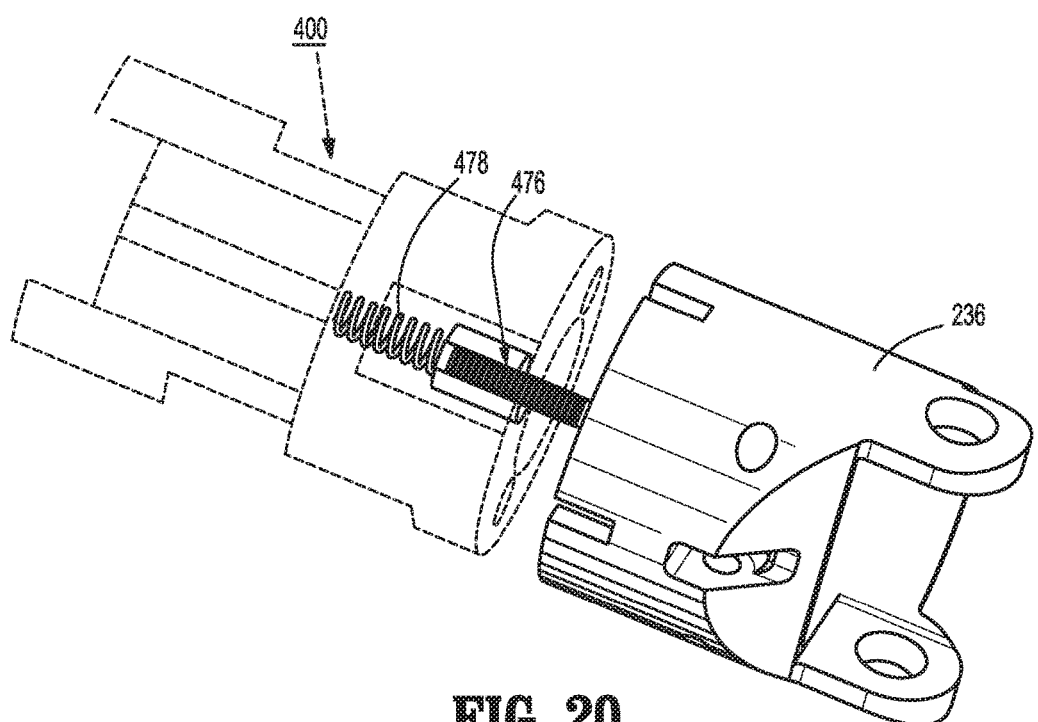
FIG. 20 is a schematic, perspective view of the end effector partially rotated relative to the shaft assembly wherein the lock mechanism is not in engagement with any of the lock notches of the shaft assembly.

As seen in FIG. 19, lock actuator 476 includes a third or intermediate position wherein biasing member 478 is partially compressed and/or biased, and wherein lock bar 472 is disposed against or rests against angled or ramped proximal surface 476c of lock actuator 476. When lock actuator 476 is in the intermediate position, lock mechanism 470 is in an automatic unlocked condition, wherein lock bar 472 is capable of moving, camming or urging, lock actuator 476 to the unlocked condition by exerting a force on angled or ramped proximal surface 476c of lock actuator 476, in a direction away from central opening 422b of coupling member 422, such as by head portion 250b of lug 250a acting on lock bar 472 if/when end effector 400 is axially separated from or moved apart from shaft assembly 200 (such as when end effector 400 and shaft assembly 200 are to be disconnected from one another).

In accordance with the present disclosure, as seen in FIGS. 7 and 8, end effector 400 may be properly connected to shaft assembly 200 in a first orientation or a second orientation (rotated approximately 90° relative to the first orientation, or any other desirable angle). The first and second orientations correspond to the location of the first annular notch 236b and the second annular notch 236c provided in distal neck housing 236 of shaft assembly 200, as described above.

In use, when coupling or connecting end effector 400 to shaft assembly 200, coupling member 422 of end effector 400 is inserted into distal neck housing 236 of shaft assembly 200, with lock actuator 476 being held (either manually or do to the contact of nose 476b of lock actuator 476 contacting a surface of distal neck housing 236 of shaft assembly 200) in the distal-most position (such that head 250b of lug 250a of shaft assembly 200 may be fully inserted into central opening 422b of coupling member 422 of end effector 400), end effector 400 is rotated relative to shaft assembly 200, along the longitudinal axis "X". As end effector 400 is rotated, when nose 476b of lock actuator 476 axially aligns with either first annular notch 236b and the second annular notch 236c of distal neck housing 236 of shaft assembly 200, lock actuator 476 may be moved to the intermediate or proximal-most position, as described above, to selectively, fixedly secure end effector 400 to shaft assembly 200 in either the first orientation or the second orientation, wherein the orientations have been manually selected and set.

When end effector 400 is secured to shaft assembly 200, distal end 242b of flexible drive cable 242 is inserted into and/or coupled to coupling socket 464a of lead or drive screw 464 of end effector 400 such that rotation of flexible drive cable 242 of shaft assembly 200 results in rotation of lead or drive screw 400.

As seen in FIGS. 8, 9 and 22-25, lower jaw 432 of jaw assembly 430 includes a drive screw 464 rotatably supported therein and extending substantially an entire length thereof. Drive screw 464 includes a female coupling socket or member 464a (or other crimp/bonded connection) supported on a proximal end thereof and being configured for receipt of a distal end 242b of flexible drive cable 242.

As seen in FIGS. 2, 7-11, 13-16, 18, 19 and 25, end effector 400 includes a flexible drive cable 242 extending proximally therefrom. In particular, flexible drive cable 242 includes a distal end 242b non-rotatably secured or connected to coupling socket 464a of drive screw 464 of end effector 400. Flexible drive cable 242 includes a proximal end 242a that is non-rotatably coupled to a cable coupler 243 which is configured for selective non-rotatable connection to first output drive shaft 246a of the first gear system of shaft assembly 200.

Flexible drive cable 242 is fabricated from a torsionally stiff and flexible material, such as, for example, stainless steel wire strands spun together into a common cable.

In this manner, since end effector 400 include flexible drive cable 242, each time a new end effector 400 is connected to shaft assembly 200 a new flexible drive cable 242 is provided and also connected to shaft assembly 200.

While flexible drive cable 242 is shown and described as being non-removably connected to coupling socket 464a of drive screw 464 of end effector 400, it is contemplated and within the scope of the present disclosure for distal end 242b of flexible drive cable 242 to be removably and non-rotatably connected to coupling socket 464*a* of drive screw 464 of end effector 400.

Figure 25:
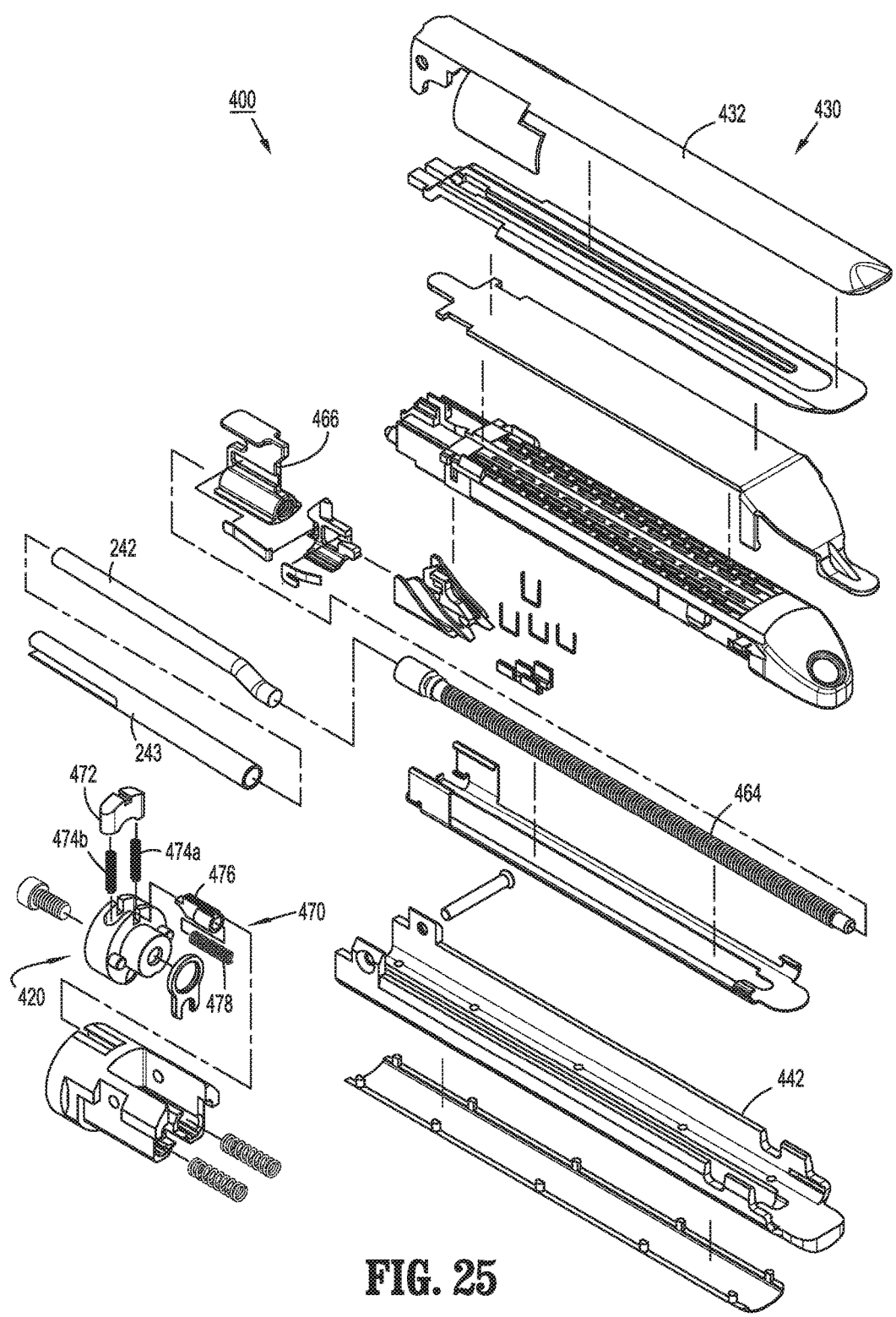
FIG. 25 is a perspective view, with parks separated, of the end effector of the present disclosure.

As seen in FIGS. 22, 24 and 25, end effector 400 includes a drive beam 466 slidably supported in lower jaw 432 of jaw assembly 430 and threadably connected to the threads of drive screw 464. Drive beam 466 includes a substantially I-shaped cross-sectional profile and is configured to approximate lower jaw 432 and upper jaw 442, and to axially displace an actuation sled 468 through lower jaw 432.

In operation, as flexible drive cable 242 is rotated, due to a rotation of first output drive shaft 246*a* of the first gear system (as described above), said rotation is transmitted, through flexible drive cable 242, to distal end 242*b* of flexible drive cable 242 and on to rotation of drive screw 464 of end effector 400. As drive screw 464 is rotated, and since drive beam 466 is constrained against rotation in jaw assembly 430, drive beam 466 is translated axially through jaw assembly 430.

It will be understood that various modifications may be made to the embodiments disclosed herein. For example, surgical instrument 100 and/or cartridge assembly 410 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. An end effector for performing a surgical function and being connectable to an electromechanical power source, the end effector comprising:
   an upper jaw and a lower jaw, at least one of the upper jaw and the lower jaw being movable in relation to the other of the upper jaw and the lower jaw, wherein the lower jaw of the end effector is configured to selectively receive a cartridge assembly;
   a drive beam slidably supported in the lower jaw and being translatable through each of the upper jaw and the lower jaw to move the lower jaw relative to the upper;
   a cartridge assembly configured for loading into the lower jaw, the cartridge assembly including an actuation sled slidably supported therein and being configured to expel at least a portion of a plurality of staples loaded in the cartridge assembly upon a distal movement of the actuation sled from a proximal-most position;
   a drive screw rotatably supported in the lower jaw, wherein the drive beam is threadably supported on the drive screw, whereby rotation of the drive screw results in axial translation of the drive beam, wherein the drive screw defines a proximal coupling socket;
   a proximal coupling hub defining a proximal facing opening;
   a lock actuator having at least a first position and a second position; and
   a lock bar supported in the proximal coupling hub and being operatively engageable by the lock actuator, the lock bar including:
      a first position in which the lock bar does not extend across the opening of the proximal coupling hub; and
      a second position in which the lock bar at least partially extends across the opening of the proximal coupling hub.

2. The end effector according to claim 1, wherein when the lock actuator is in the first position the lock bar is in the first position, and, wherein when the lock actuator is in the second position the lock bar is engaged by the lock actuator and urged by the lock actuator to the second position.

3. The end effector according to claim 1, wherein at least one of the lock actuator is biased to the second position, and the lock bar is biased to the first position.

4. The end effector according to claim 1, wherein the lock actuator includes an intermediate position between the first position and the second position thereof, wherein in the intermediate position, an angled camming surface of the lock actuator is in contact with the lock bar such that the lock bar is disposed at an intermediate position between the first position and the second position thereof.

5. The end effector according to claim 1, further comprising:
   a flexible drive cable coupled to the coupling socket of the drive screw, wherein the flexible drive cable receives rotational forces and transmits said rotational forces to the drive screw to actuate the end effector.

6. An end effector for performing a surgical function and configured to couple to a shaft assembly, the end effector comprising:
   a coupling hub defining an opening;
   a lock actuator movable between a first actuator position and a second actuator position and being biased into the second actuator position; and
   a lock bar movable between a first bar position and a second bar position in which the lock bar extends at least partially across the opening, the lock bar being biased into the first bar position, such that when the lock actuator is in the second actuator position, the lock actuator moves the lock bar into the second bar position and when the lock actuator is in the first position the lock bar is moved into the first position.

7. The end effector according to claim 6, further comprising:
   an upper jaw; and
   a lower jaw, wherein at least one of the upper jaw or the lower jaw is movable relative to each other.

8. The end effector according to claim 7, wherein the lower jaw is configured to receive a cartridge assembly.

9. The end effector according to claim 8, wherein the cartridge assembly includes:
   a plurality of staples; and
   an actuation sled slidably supported therein and configured to eject at least one staple of the plurality of staples upon movement of the actuation sled.

10. The end effector according to claim 6, further comprising:
    a drive screw rotatably supported in the lower jaw; and
    a drive beam slidably supported in the lower jaw and threadably coupled to the drive screw, wherein rotation of the drive screw moves the drive beam through each of the upper jaw and the lower jaw to move at least one of the lower jaw or the upper jaw.

11. The end effector according to claim 10, wherein the drive screw defines a proximal coupling socket.

12. The end effector according to claim 11, further comprising:

a flexible drive cable coupled to the coupling socket, wherein the flexible drive cable is configured to transmit a rotational force to the drive screw to actuate the end effector.

13. The end effector according to claim 6, wherein the coupling hub is configured to couple to a shaft assembly and the lock actuator is configured to engage a slit defined in the shaft assembly.

14. A surgical device comprising:
a shaft assembly including a distal portion defining a notch therein; and
an end effector including:
  a coupling hub defining an opening, the coupling hub configured to couple to the distal portion of the shaft;
  a lock actuator configured to engage the notch, the lock actuator movable between a first actuator position and a second actuator position when engaged with the notch and being biased into the second actuator position; and
  a lock bar movable between a first bar position and a second bar position in which the lock bar extends at least partially across the opening, the lock bar being biased into the first bar position, such that when the lock actuator is in the second actuator position, the lock actuator moves the lock bar into the second bar position and when the lock actuator is in the first position the lock bar is moved into the first position.

15. The surgical device according to claim 14, wherein the shaft assembly further includes a coupling lug configured to be inserted into the opening of the end effector and to engage the lock bar.

16. The surgical device according to claim 14, the end effector further comprising:
an upper jaw; and
a lower jaw, wherein at least one of the upper jaw or the lower jaw is movable relative to each other.

17. The surgical device according to claim 16, wherein the lower jaw is configured to receive a cartridge assembly.

18. The surgical device according to claim 17, wherein the cartridge assembly includes:
a plurality of staples; and
an actuation sled slidably supported therein and configured to eject at least one staple of the plurality of staples upon movement of the actuation sled.

19. The surgical device according to claim 16, the end effector further comprising:
a drive screw rotatably supported in the lower jaw; and
a drive beam slidably supported in the lower jaw and threadably coupled to the drive screw, wherein rotation of the drive screw moves the drive beam through each of the upper jaw and the lower jaw to move at least one of the lower jaw or the upper jaw.

20. The end effector according to claim 19, wherein the drive screw defines a proximal coupling socket.

\* \* \* \* \*